United States Patent [19]

Jung et al.

[11] Patent Number: 5,235,061
[45] Date of Patent: Aug. 10, 1993

[54] FUNGICIDAL (1H-1,2,4-TRIAZOLYL)DISILAALKANES

[75] Inventors: Il Nam Jung; Bok Ryul Yoo, both of Seoul; Mi Suk Kim, Daejon; Seung Ho Yoen, Kyungki-Do, all of Rep. of Korea

[73] Assignee: Korea Institute of Science and Technology, Seoul, Rep. of Korea

[21] Appl. No.: 871,921

[22] Filed: Apr. 21, 1992

[30] Foreign Application Priority Data

Apr. 23, 1991 [KR]  Rep. of Korea ................. 6503/1991

[51] Int. Cl.$^5$ ............................................. C07F 7/18
[52] U.S. Cl. .................................................. 548/110
[58] Field of Search ......................................... 548/110

[56] References Cited

U.S. PATENT DOCUMENTS 4,729,986  3/1988  Olson ................................. 548/110

Primary Examiner—Patricia L. Morris
Attorney, Agent, or Firm—Townsend and Townsend

[57] ABSTRACT

This invention relates to (1H-1,2,4-triazolyl)disilaalkanes as represented by formula I, their preparation, and their use in controlling fungus diseases of living plants.

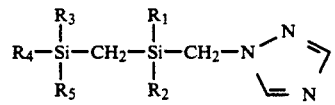

wherein $R_1$, $R_2$, $R_3$, $R_4$, and $R_5$ can be independently lower alkyl, vinyl, allyl, benzyl, or substituted phenyl such as para-fluorophenyl, para-chlorophenyl, para-enthoxyphenyl, and biphenyl.

1 Claim, No Drawings

FUNGICIDAL (1H-1,2,4-TRIAZOLYL)DISILAALKANES

BACKGROUND OF THE INVENTION

1. Field of the Invention

This invention relates to (1H-1,2,4-triazolyl)disilaalkanes as represented by formula I, their preparation, and their use in controlling fungus diseases of living plants:

$$\begin{array}{c} R_3 \quad\quad R_1 \\ | \quad\quad\quad | \\ R_4-Si-CH_2-Si-CH_2-N \\ | \quad\quad\quad | \\ R_5 \quad\quad R_2 \end{array} \underset{N}{\overset{N}{\diagdown}}\!\!\!\diagup \quad (I)$$

wherein $R_1$, $R_2$, $R_3$, $R_4$, and $R_5$ can be independently lower alkyl, vinyl, allyl, benzyl, or substituted phenyl such as para-fluorophenyl, para-chlorophenyl, para-ethoxyphenyl, and biphenyl.

2. Description of the Prior Art

Since the late 1960's, the derivatives of azoles have been known to be useful for the control of plant diseases (Deutsche. Med. Wochenschrift, 4,1356–1364 (1969)). U.S. Pat. No. 3,692,798 discloses later the organosilylimidazoles of the following formula:

$$\begin{array}{c} R_1 \\ | \\ R_2-Si-CH_2-N \\ | \\ R_3 \end{array} \!\!\!\diagup\!\!\!\!\!\diagdown N$$

wherein $R_1$, $R_2$, and $R_3$ can be lower alkyl and phenyl. It is stated that these compounds are useful as antimicrobial agents.

German Patent No. DE 3,000,140 discloses silyl ethers of the formula:

$$\begin{array}{c} OSi\,R_3 \\ | \\ Ar-O-CH-CH-CMe_3 \\ | \\ N \diagdown \\ \diagup \quad X \\ N \end{array}$$

wherein Ar can be substituted phenyl, X can be CH or N, and R can be phenyl or lower alkyl. It is taught that organosilyl imidazoles or triazoles are useful as agricultural fungicides.

U.S. Pat. No. 4,510,136 discloses organosilyl group substituted at beta carbon to triazol ring represented by the following formula:

$$\begin{array}{c} Q_1 \\ \diagdown \\ R_1 \quad\quad N \\ | \\ R_2-Si-CH_2-N \\ | \quad\quad\quad \diagdown \\ R_2 \quad\quad N-Q_2 \end{array}$$

wherein $R_1$, $R_2$, and $R_3$ can be independently lower alkyl or substituted phenyl, and $Q_1$ and $Q_2$ can be independently H or $CH_3$. It is stated that the organosilyl triazoles have strong fungicidal activities and can be used to control plant fungus diseases.

The organosilyl triazoles with aromatic substituents on silicon have better fungicidal activities than the organosilyltriazoles with alkyl substituents on silicon. The triazoles with phenyl groups on silicon, having fluorine, trifluoromethyl, ethoxy, or phenyl substituent at para position show better activities than those having chloro or methyl substituent at para position.

Japan patent No. 63-5092 discloses organosilyl bistriazoles of the following formula:

$$\begin{array}{c} CH_3 \\ | \\ X-\!\!\bigcirc\!\!-Si-CH_2-N\!\!\diagdown\!\!\!\!\!\diagup N \\ | \\ CH_2-N-N \\ \diagdown\!\!\!\!\!\diagup \\ N \end{array}$$

wherein X can be H, halogen, alkoxy, phenyl, substituted phenyl with halogen or lower alkyl group. It is taught that the organosilyl bistriazoles have fungicidal activities.

German patent DE 3,723,246 discloses organosilyl compounds having triazole and thiophene groups of the formula:

$$\begin{array}{c} CH_3 \\ | \\ X-\!\!\diagup\!\!\!\!\diagdown\!\!-Si-CH_2N\!\!\diagdown\!\!\!\!\!\diagup N \\ S \quad\quad | \\ R \end{array}$$

wherein X can be alkyl or halogen and R can be phenyl or substituted phenyl.

U.S. Pat. Nos. 4,530,922 and 4,729,982 also disclose the silyltriazole compounds which are similar to the compounds disclosed in U.S. Pat. No. 4,510,136 except that alkenyl or ethynyl groups substituted on silicon instead of the methyl group. It is also stated that the compounds disclosed in the patents having thiol or thiocyanide groups substituted on the triazole ring are active.

BRIEF DESCRIPTION OF THE INVENTION

We have found that (1H-1,2,4-triazolyl)disilaalkanes as represented by formula I, have fungicidal activities and can be used to control plant fungus diseases:

$$\begin{array}{c} R_3 \quad\quad R_1 \\ | \quad\quad\quad | \\ R_4-Si-CH_2-Si-CH_2-N \\ | \quad\quad\quad | \\ R_5 \quad\quad R_2 \end{array} \underset{N}{\overset{N}{\diagdown}}\!\!\!\diagup \quad (I)$$

wherein $R_1$, $R_2$, $R_3$, $R_4$, and $R_5$ can be independently lower alkyl, vinyl, allyl, benzyl, or substituted phenyl such as para-fluorophenyl, para-chlorophenyl, para-ethoxyphenyl, and biphenyl.

DESCRIPTION OF PREFERRED EMBODIMENTS

This invention relates to novel compounds of (1H-1,2,4-triazolyl)disilaalkanes as represented by formula I:

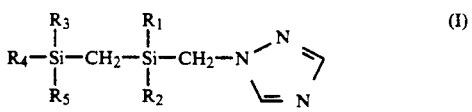

wherein $R_1$, $R_2$, $R_3$, $R_4$, and $R_5$ can be independently lower alkyl, vinyl, allyl, benzyl, or substituted phenyl such as para-fluorophenyl, para-chlorophenyl, para-ethoxyphenyl, and biphenyl.

The compounds of the general formula I can be prepared by reacting the compounds of the general formula II with triazole sodium salt in DMF solution:

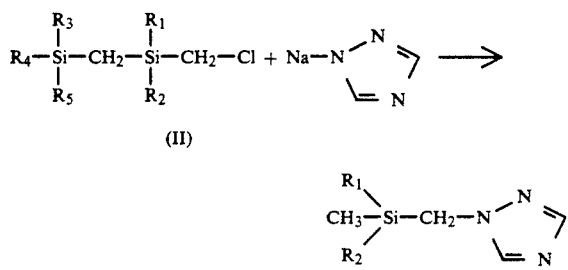

wherein $R_1$, $R_2$, $R_3$, $R_4$, and $R_5$ can be independently lower alkyl, vinyl, allyl, benzyl, or substituted phenyl such as para-fluorophenyl, para-chlorophenyl, para-ethoxyphenyl, and biphenyl.

The compounds of the general formula II can be prepared by reacting Grignard reagents as represented by the general formula VI or organolithium compounds with chloromethyl containing disilaalkanes as represented by the general formula III.

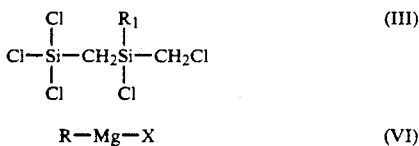

In general formula III, $R_1$ can be chlorine atom or methyl. In general formula VI, R can be lower alkyl, vinyl, allyl, benzyl, or substituted phenyl such as para-fluorophenyl, para-chlorophenyl, para-ethoxyphenyl, and biphenyl and X represents chloro atom or bromo atom. The Si—Cl bonds of the chlorodisilaalkanes react with organolithium or Grignard reagents to introduce alkenyl and/or aryl groups according to literature procedures, leaving the C—Cl bond uneffected (Zh. Obschch. Khim., 9, 1977 (1969)). For the silanes containing more than two Si—Cl bonds, stepwise replacements are possible.

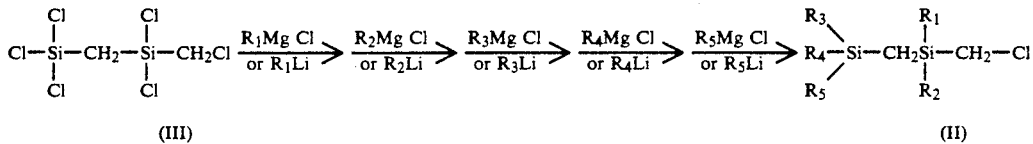

Preferred solvents for these reactions include ethers such as diethylether, 1,2-dimethoxyethane, and tetrahydrofuran. The reaction of the chlorosilanes with Grignard reagents or aryllithium may be conducted at any temperature of from −20° C. up to 50° C., but bellow 25° C. is preferred. Instead of preforming an aryllithium reagent, an arylbromide may be treated with alkyllithium in an inert solvent such as hexane at a temperature of −78° C. to 0° C. and then combined the obtained product with a chlorosilane such as chloromethylmethylvinylchlorosilane or chloromethylmethyldichlorosilane in ether solution. In order to couple the last chlorine on silicon with aromatic group, aryl bromide and n-butyllithium may be used instead of the aryl Grignard reagent or aryllithium compound. Bromine lithium exchange proceeds and the resulting aryllithium reacts with the chlorosilane (H. Gilmann, "Advances in Organometallic Chemistry, "Vol. 7. Academic Press, New York, 1968).

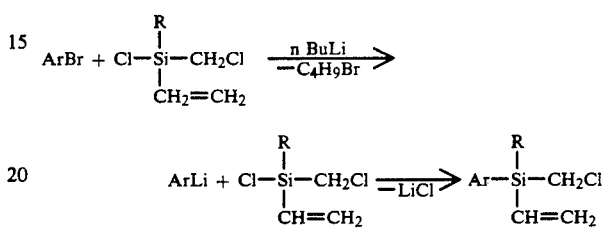

The chloromethyl containing disilaakanes as represented by the general formula III can easily be prepared by the chlorination reaction of the corresponding methyl compounds which are obtained from the direct reactions of chloromethyl containing silanes with silicon in the presence of copper catalyst (I. N. Jung et al, Korean Patent Application No. 1055 filed Jan. 22, 1991).

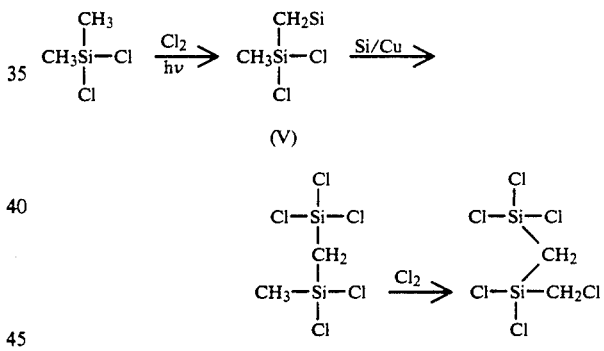

The chloromethyl containing disilaalkane compounds of the general formula II can also be prepared by another method as the following. The chloromethyl containing chlorosilanes as represented by the general formula V may be reacted with Grignard reagents as represented by the general formula VI to give chloromethylsilanes as represented by the general formula IV. The chloromethylsilanes as represented as in general formula IV can be converted to a Grignard reagent by reacting it with magnesium metal and followed by coupling again with chloromethyl containing chlorosilanes to give the disilaalkanes.

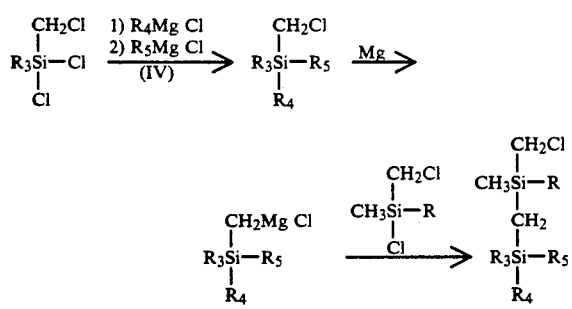

In the above reaction R, $R_3$, $R_4$, and $R_5$ can be independently lower alkyl, vinyl, allyl, benzyl, or substituted phenyl such as para-fluorophenyl, para-chlorophenyl, para-ethoxyphenyl, and biphenyl.

The disilaalkanes substituted by triazole, as represented by the formula I, can be prepared from choromethyl containing disilaalkanes of formula II and 1,2,4-triazole sodium salt. Lithium and potassium triazole salts may also be used. Bromomethyl or iodomethyl containing disilaalkanes may be used instead of chloromethyl compounds. The highest yield was obtained with about 5–10% excess of the used triazole salt amount. Suitable solvents include polar aprotic solvents such as dimethylformamide, dimethylsulfoxide, or acetonitrile. The reaction temperature can vary between 0° C. and 100° C. The reaction can be conducted under elevated pressure, but it is generally operated at atmospheric pressure. The optimum temperature and reaction time will vary with the concentration and choice of reagents, and especially with choice of solvent. For example, the reaction of iodomethylmethylvinyl (4-fluorophenyl)silane with 1,2,4-triazole sodium salt at 1 molar concentration in dimethylformamide gives almost complete conversion within 4 hours at 60° C. Progress of the reaction can be followed by working up aliquots for gas chromatography analysis and following the disappearance of the silane and the appearance of new peak due to the product.

Higher reaction temperature than 80° C. gives poor yields due to polymerization of vinylsilanes. The reaction of triazole displacement gives better yields and proceeds faster for iodomethylsilane than the corresponding chloromethylsilane. Chloromethylsilane may be converted to the corresponding iodomethylsilanes by chlorine-iodine exchange reaction using sodium iodide in acetone solution. It is often advantageous to exchange chloride for iodide before doing the triazole displacement (D. R. Baker, J. G. Fenyes, W. K. Moberg, and B. Cross Ed., "Synthesis and Chemistry of Agrochemicals", American Chemical Society, Washington, D.C., 1987).

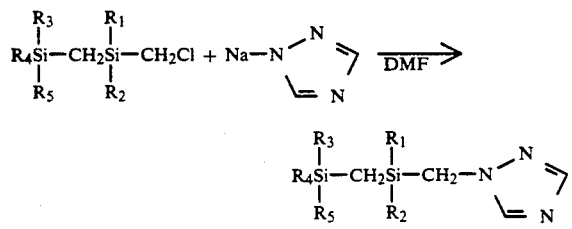

In the following examples, temperatures are reported in degrees Celsius. Abbreviations for nuclear magnetic resonance(nmr) spectra are s=singlet, d=doublet, t=triplet, m=multiplet; peak positions are reported as parts per million on the basis of the internal tetramethylsilane. Infrared(ir) peak positions are given in reciprocal centimeters(cm$^{-1}$). Ether refers to diethylether.

EXAMPLE 1

Preparation of
1-chloro-2,4-bis(4-chlorophenyl)-2,4-dimethyl-2,4-disilapentane i) To a 500 ml, three neck, round bottomed flask equipped with a mechanical stirrer, a dropping funnel, and a reflux condenser, were added 26.0 ml (0.2 mole) of chloromethyldimethylchlorosilane and 200 ml of tetrahydrofurane. 220 ml (1.0M in THF) of 4-chlorophenyl Grignard solution was added dropwise through the additional funnel at the room temperature with stirring. After addition was completed, the reaction mixture was stirred for 2 hours at room temperature, quenched carefully with saturated aqueous ammonium chloride after confirming that all the starting material were reacted by gas chromatography technique, and then filtered. The aqueous layer was extracted three times with ether. The ether solutions were combined with the organic layer and dried over magnesium sulfate. The solvents were evaporated and the residue was 30g (92% yield) of chloromethyl(4-chlorophenyl) dimethyl silane.

ii) To a 100 ml, three neck, round bottomed flask equipped with a dropping funnel, and a reflux condenser, were added 3.0 g of magnesium species and 0.5 g of iodine. After 5 ml of tetrahydrofurane was added therein, 0.5 g of total chloromethyl(4-chlorophenyl)-dimethylsilane (15.5 g (92%), 65 mmol) synthesized from procedure i) was firstly added through the dropping funnel. The mixture was maintained at the temperature of 35° to 45° C. with heat gun. The remaining chloromethyl(4-chlorophenyl)dimethylsilane was continuously dropwise added to obtain Grignard solution of chloromethyl(4-chlorophenyl)dimethylsilane.

iii) To a 250 ml, three neck, round bottomed flask equipped with a mechanical stirrer, a dropping funnel, and a reflux condenser were added 6.4 ml (50 mmol) of chloromethylmethyl dichlorosilane and 100 ml of tetrahydrofuran. 55 ml (10% exess) of 4-chlorophenyl Grignard solution (1M in THF) was dropwise added through the dropping funnel for 1 hr and 30 minutes, and stirred for 2 hrs. After confirming by gas chromatography to complete the reaction, the Grignard solution of chloromethyl(4-chlorophenyl)dimethylsilane prepared from procedure ii) was added and stirred for 3 hrs. After confirming by gas chromatography to complete the reaction, the reaction product was treated in the same manner as procedure i) to obtain 15.1 g of the mixture of the reaction products, which by NMr analysis was ascertained that 1-chloro-2,4-bis(4-chlorophenyl)-2,4-dimethyl-2,4-disilapentane was produced.

EXAMPLE 2

Preparation of
1-chloro-4-(4-fluorobenzyl)-2-(4-fluorophenyl)-2,4-dimethyl-2,4-disilapentane i) To a 250 ml, three neck, round bottomed flask equipped with a reflux condenser and a dropping funnel were added 7.3 g of magnesium pieces (0.3 mole, 50% exess), 0.5 g of iodine and 20 ml of tetrahydrofuran. Through the dropping funnel was firstly added 1 ml of Qotal 4-fluorobenzyl chloride (24 ml, 0.2 mole) and heated with heat gun to maintain at the temperature of 35° to 45° C. The remaining product was added to obtain the 4-fluorobenzyl Grignard solution. In the same apparatus and procedures as Example 1-i) were reacted 26 ml (0.2 mole) of chloromethyldimethylchlorosilane and 4-fluorobenzyl Grignard solution (0.2 mole) as previously synthesized, and the obtained reaction product was treated to obtain 38 g of chloromethyl(4-fluorobenzyl)dimethylsilane (75%).

ii) In the same apparatus and procedures as Example 1 were reacted 6.4 g of chloromethylmethyldichlorosilane, 25 ml of 4-fluorobenzyl Grignard solution (2M in ether) and the prepared Grignard solution of chloromethyl(4-fluorobenzyl)dimethylsilane from the above procedure i) [15 g of the reaction product containing chloromethyl(4-fluorobenzyl) dimethylsilane (75%, 52 mmol), 1.9 g of magnesium pieces, and 0.3 g of iodine] in turn to treat the reaction product. After separating them by using silica gel column eluent: hexane), 5.9 g of 1-chloro-4-(4-fluorobenzyl)-2-(4-fluorophenyl)-2,4-dimethyl-2,4-disilapentane was obtained.

EXAMPLE 3

Preparation of
1-chloro-2-(4-fluorophenyl)-2,4-dimethyl-4-(4-phenylphenyl)-2,4-disilapentane.

i) In the same apparatus and procedures as Example 2-i) were reacted 18.7 g (80 mmol) of 4-bromobiphenyl, 4.8 g of magnesium and 0.7 g of iodine to prepare 4-phenylphenyl Grignard solution. In the same apparatus and procedures were reacted 10.4 ml (80 mmol) of chloromethyldimethylchlorosilane and the prepared 4-phenylphenyl Grignard solution to treat the reaction product. After separating them by using silica gel column (eluent: hexane), 12 g of chloromethyldimethyl(4-phenylphenyl)silane (92%) was obtained.

ii) In the same apparatus and procedures as Example 1 were reacted 3.8 ml (30 mmol) of chloromethylmethyldichlorosilane, 15 ml of 4-fluorophenyl Grignard solution (2M in ether) and Grignard solution of chloromethyldimethyl(4-phenylphenyl)silane [12 g of chloromethyldimethyl (4-biphenyl)silane (92%, 42 mmol), 2.1 g of magnesium pieces, 0.5 g of I$_2$] as synthesized from the above procedure i) in turn to treat the reaction product. 17 g of the mixture of the reaction products was obtained, which was confirmed by NMR analysis to be produced 1-chloro-2-(4-fluorophenyl)-2,4-dimethyl-4-(4-phenylphenyl)-2,4-disilapentane.

EXAMPLE 4

Preparation of
1-chloro-2-(4-ethoxyphenyl)-4-(4-methoxyphenyl)-2,4-dimethyl-2,4-disilapentane i) In the same apparatus and procedures as Example 2-i) were reacted 18.8 g (0.15 mmol) of 4-bromoanisole and 5 g of magnesium pieces to prepare 4-methoxyphenyl Grignard solution. In the same method as Example 1-i) were reacted 19.7 ml (0.15 mmol) of chloromethyldimethylchlorosilane and 4-methoxyphenyl Grignard solution as previously synthesized and the reaction product was treated to obtain 28.4 g (94%) of chloromethyl (4-methoxyphenyl) dimethylsilane.

ii) In the same method as Example 1 were reacted 6.4 ml (50 mmol) of chloromethylmethyldichlorosilane, 4-ethoxyphenyl Grignard solution [12.1 g (60 mmol) of 4-bromophenetole, 2.4 g of magnesium pieces], Grignard solution of chloromethyl(4-methoxyphenyl)dimethylsilane which was synthesized from procedure i) [13.7 g (94%, 60 mmol) of chloromethyl (4-methoxyphenyl)dimethylsilane, 2.4 g of magnesium pieces, 0.5 g of iodine] is turn to treat the reaction product. 24 g of the mixture of the reaction products was obtained, which was confirmed by NMR analysis to be produced 1-chloro-2-(4-ethoxyphenyl)-4-(4-methoxyphenyl)-2,4-dimethyl-2,4-disilapentane.

EXAMPLE 5

Preparation of
1-chloro-2-(4-fluorophenyl)-2,4,4-trimethyl-2,4-disilapentane

To a 250 ml, three neck, round bottomed flask equipped with a dropping funnel, a reflux condenser, and a mechanical stirrer were added 2.0 g (12 mmol) of chloromethylmethyldichlorosilane and 30 ml of tetrahydrofuran. 6.4 ml of 4-fluorophenyl Grignard solution (2M in ether) was dropwise added in the ice-bath through the dropping funnel for 30 minutes, and then stirred at the room temperature for 1 hr. 12 ml of trimethylsilylmethyl Grignard solution (1M in ether) was dropwise added and refluxed for 3 hrs. In the same method as Example 1 was treated the reaction product to obtain 3.3 g of 1-chloro-2-(4-fluorophenyl)-2,4,4-trimethyl-2,4-disilapentane.

EXAMPLE 6

Preparation of
1-chloro-2,2-bis(4-fluorophenyl)-4,4-dimethyl-2,4-disilapentane

To a 250 ml, three neck, round bottomed flask equipped with a reflux condenser and a dropping funnel were added 2.1 g (11.4 mmol) of chloromethyltrichlorosilane and 50 ml of tetrahydrofuran. 11.4 ml of 4-fluorophenyl Grignard solution (2M in ether) was added at the room temperature through the dropping funnel and refluxed for 3 hrs, and then, 11.4 ml of trimethylsilylmethyl Grignard solution (1M in ether) was transferred to the dropping funnel to dropwisely add for 5 minutes and reflux for 7 hrs, after confirming by gas chromatography (GC) to complete the reaction, and treating the reaction product in the same method as Example 1, 1.2 g of 1-chloro-2,2-bis(4-fluorophenyl)-4,4-dimethyl-2,4-disilapentane was obtained, by separating them by silica gel column (eluent: hexane).

The compounds according to the procedure described in Example 1 through 5 are listed in Table 1.

TABLE 1

$$CH_3-\underset{\underset{R_2}{|}}{\overset{\overset{CH_3}{|}}{Si}}-CH_2-\underset{\underset{R_1}{|}}{\overset{\overset{CH_3}{|}}{Si}}-CH_2Cl$$

| R$_1$ | R$_2$ | Example No. |
|---|---|---|
| 4-fluorophenyl | CH$_3$ | 5 |
| 4-methoxyphenyl | CH$_3$ | |
| 4-phenylphenyl | CH$_3$ | |
| 4-chlorophenyl | 4-fluorophenyl | |
| 4-ethoxyphenyl | 4-fluorophenyl | |
| 4-fluorophenyl | 4-fluorophenyl | 6 |
| 4-methoxyphenyl | 4-chlorophenyl | |
| 4-chlorophenyl | 4-chlorophenyl | 1 |
| 4-fluorophenyl | 4-chlorophenyl | |
| 4-phenylphenyl | 4-chlorophenyl | |
| 4-methoxyphenyl | 4-methoxyphenyl | |
| 4-ethoxyphenyl | 4-methoxyphenyl | |
| 4-phenylphenyl | 4-methoxyphenyl | |

TABLE 1-continued $$CH_3-\underset{\underset{R_2}{|}}{\overset{\overset{CH_3}{|}}{Si}}-CH_2-\underset{\underset{R_1}{|}}{\overset{\overset{CH_3}{|}}{Si}}-CH_2Cl$$

| R₁ | R₂ | Example No. |
|---|---|---|
| 4-fluorophenyl | 4-ethoxyphenyl | |
| 4-methoxyphenyl | 4-ethoxyphenyl | 4 |
| 4-phenylphenyl | 4-ethoxyphenyl | |
| 4-ethoxyphenyl | 4-phenylphenyl | |
| 4-phenylphenyl | 4-phenylphenyl | |
| 4-fluorophenyl | 4-phenylphenyl | 3 |
| 4-fluorophenyl | 4-fluorobenzyl | 2 |
| 4-chlorophenyl | 4-fluorobenzyl | |
| 4-methoxyphenyl | 4-fluorobenzyl | |

EXAMPLE 7

1-chloro-4-(4-chlorophenyl)-2,2-bis(4-methoxyphenyl)-4-methyl-2,4-disilapentane

To 5.5 g (30 mmol) of chloromethyltrichlorosilane was added 4-methoxyphenyl Grignard solution (11.2 g (60 mmol) of 4-bromoanisole, 2.4 g of magnesium pieces, and 0.5 g of iodine were reacted in the same method as Example 2-i)) at the room temperature to be reacted at the temperature of from 35° to 40° C. for 4 hrs. Then, the Grignard solution of chloromethyl(4-chloromethyl)dimethylsilane which was prepared in Example 1 (8.3 g (92%, 35 mmol) of chloromethyl(4-chlorophenyl)dimethylsilane, 1.2 g of magnesium pieces, and 0.7 g of iodine were reacted in the same method as Example 1-i)) was reacted at the temperature of 35° C. for 6 hrs to obtain 18 g of the mixture of the reaction products, which was confirmed by NMR analysis to be produced 1-chloro-4-(4-chlorophenyl)-2,2-bis(4-methoxyphenyl)-4-methyl-2,4-disilapentane.

EXAMPLE 8

Preparation of 1-chloro-2,4-bis(4-fluorophenyl)-4-methyl-2-(4-phenylphenyl)-2,4-disilapentane i) 32.9 ml (0.25 mmol) of chloromethyldimethylchlorosilane and 125 ml of 4-fluorophenyl Grignard solution(2M in ether) were reacted in the same method as Example 1-i) to obtain 46 g of chloromethyl(4-fluorophenyl)dimethylsilane.

ii) To 5.5 g (30 mmol) of chloromethyltrichlorosilane were added 15 ml of 4-fluorophenyl Grignard solution (2M in ether) and 4-phenylphenyl Grignard solution (6.9 g (30 mmol) of 4-bromophenyl, 1.4 g of magnesium pieces, and 0.5 g of iodine were reacted as in Example 2-i)) in turn and reacted under reflux for 4 hrs. Then, the Grignard solution of chloromethyl(4-fluorophenyl)dimethylsilane which was prepared in the procedure i) [7.1 g (94%, 33 mmol) of chloromethyl(4-fluorophenyl) dimethylsilane, 1.5 g of magnesium pieces, and 0.6 g of iodine] were reacted in the same method as Example 1-ii) was added and reacted under reflux for 5 hrs to obtain 21 g of the compound containing 1-chloro-2,4-bis(4-fluorophenyl)-4-methyl-2-(4-phenylphenyl)-2,4-disilapentane.

EXAMPLE 9

Preparation of 1-chloro-2,2-bis(4-chlorophenyl)-4-(4-ethoxyphenyl)-4-methyl-2,4-disilapentane i) In the same method as Example 2-i) were reacted 17 ml (0.12 mole) of 4-bromophenetole, 4.9 g of magnesium pieces, and 0.7 g of iodine to prepare 4-ethoxyphenyl Grignard solution. 15.8 ml (0.12 mmol) of chloromethyldimethylchlorosilane and 4-ethoxyphenyl Grignard solution as previously prepared were reacted in the same method as Example 1-i) to obtain 25.5 g (74%) of chloromethyl(4-ethoxyphenyl)dimethylsilane.

ii) 60 ml of 4-chlorophenyl Grignard solution (1M in THF) was added to 5.5 g (30 mmol) of chloromethyltrichlorosilane to be readed at 35° C. for 7 hrs, in the same apparatus and procedures as Example 6. The Grignard solution of chloromethyl(4-ethoxyphenyl)dimethylsilane which was synthesized from the procedure i) [12.3 g (74%, 40 mmol) of chloromethyl (4-ethoxyphenyl)-dimethylsilane, 1.8 g of magnesium pieces and 0.5 g of iodine] was added therein to be reacted at 40° C. for 5 hrs. 18.2 g of the mixture of the reaction products was obtained, which was confirmed by NMR analysis to be produced 1-chloro-2,2-bis(4-chlorophenyl)-4-(4-ethoxyphenyl)-4-methyl-2,4-disilapentane.

The compounds prepared according to the procedure described in Example 7 through 9 are listed in Table 2.

TABLE 2

$$CH_3-\underset{\underset{R_3}{|}}{\overset{\overset{CH_3}{|}}{Si}}-CH_2-\underset{\underset{R_2}{|}}{\overset{\overset{CH_3}{|}}{Si}}-CH_2Cl$$

| R₁ | R₂ | R₃ | Example No. |
|---|---|---|---|
| 4-methoxyphenyl | 4-methoxyphenyl | CH₃ | 7 |
| 4-methoxyphenyl | 4-phenylphenyl | CH₃ | |
| 4-methoxyphenyl | 4-ethoxyphenyl | CH₃ | |
| 4-fluorophenyl | 4-chlorophenyl | CH₃ | |
| 4-fluorophenyl | 4-methoxyphenyl | CH₃ | |
| 4-fluorophenyl | 4-fluorophenyl | CH₃ | |
| 4-phenylphenyl | 4-fluorophenyl | CH₃ | |
| 4-chlorophenyl | 4-chlorophenyl | CH₃ | |
| 4-chlorophenyl | 4-methoxyphenyl | CH₃ | |
| 4-chlorophenyl | 4-phenylphenyl | CH₃ | |
| 4-ethoxyphenyl | 4-chlorophenyl | CH₃ | |
| 4-ethoxyphenyl | 4-ethoxyphenyl | CH₃ | |
| 4-ethoxyphenyl | 4-phenylphenyl | CH₃ | |
| 4-methoxyphenyl | 4-chlorophenyl | 4-fluorophenyl | |
| 4-methoxyphenyl | 4-methoxyphenyl | 4-fluorophenyl | |
| 4-ethoxyphenyl | 4-ethoxyphenyl | 4-fluorophenyl | |
| 4-methoxyphenyl | 4-phenylphenyl | 4-fluorophenyl | |
| 4-chlorophenyl | 4-chlorophenyl | 4-fluorophenyl | |
| 4-chlorophenyl | 4-ethoxyphenyl | 4-fluorophenyl | |
| 4-phenylphenyl | 4-fluorophenyl | 4-fluorophenyl | 8 |
| 4-fluorophenyl | 4-fluorophenyl | 4-fluorophenyl | |
| 4-fluorophenyl | 4-chlorophenyl | 4-fluorophenyl | |
| 4-fluorophenyl | 4-ethoxyphenyl | 4-fluorophenyl | |
| 4-ethoxyphenyl | 4-phenylphenyl | 4-fluorophenyl | |
| 4-methoxyphenyl | 4-methoxyphenyl | 4-chlorophenyl | |
| 4-methoxyphenyl | 4-ethoxyphenyl | 4-chlorophenyl | |
| 4-fluorophenyl | 4-chlorophenyl | 4-chlorophenyl | |
| 4-fluorophenyl | 4-fluorophenyl | 4-chlorophenyl | |
| 4-fluorophenyl | 4-ethoxyphenyl | 4-chlorophenyl | |
| 4-chlorophenyl | 4-methoxyphenyl | 4-chlorophenyl | |
| 4-chlorophenyl | 4-chlorophenyl | 4-chlorophenyl | |
| 4-phenylphenyl | 4-fluorophenyl | 4-chlorophenyl | |
| 4-ethoxyphenyl | 4-ethoxyphenyl | 4-chlorophenyl | |
| 4-ethoxyphenyl | 4-chlorophenyl | 4-chlorophenyl | |
| 4-methoxyphenyl | 4-phenylphenyl | 4-methoxyphenyl | |
| 4-methoxyphenyl | 4-methoxyphenyl | 4-methoxyphenyl | |
| 4-methoxyphenyl | 4-ethoxyphenyl | 4-methoxyphenyl | |

TABLE 2-continued $$CH_3-\underset{\underset{R_3}{|}}{\overset{\overset{CH_3}{|}}{Si}}-CH_2-\underset{\underset{R_2}{|}}{\overset{\overset{CH_3}{|}}{Si}}-CH_2Cl$$

| R₁ | R₂ | R₃ | Example No. |
|---|---|---|---|
| 4-chlorophenyl | 4-chlorophenyl | 4-methoxyphenyl | |
| 4-chlorophenyl | 4-methoxyphenyl | 4-methoxyphenyl | |
| 4-ethoxyphenyl | 4-fluorophenyl | 4-methoxyphenyl | |
| 4-ethoxyphenyl | 4-ethoxyphenyl | 4-methoxyphenyl | |
| 4-fluorophenyl | 4-fluorophenyl | 4-methoxyphenyl | |
| 4-fluorophenyl | 4-methoxyphenyl | 4-methoxyphenyl | |
| 4-fluorophenyl | 4-chlorophenyl | 4-methoxyphenyl | |
| 4-phenylphenyl | 4-ethoxyphenyl | 4-methoxyphenyl | |
| 4-phenylphenyl | 4-chlorophenyl | 4-methoxyphenyl | |
| 4-ethoxyphenyl | 4-ethoxyphenyl | 4-ethoxyphenyl | |
| 4-methoxyphenyl | 4-methoxyphenyl | 4-ethoxyphenyl | |
| 4-methoxyphenyl | 4-ethoxyphenyl | 4-ethoxyphenyl | |
| 4-chlorophenyl | 4-chlorophenyl | 4-ethoxyphenyl | 9 |
| 4-chlorophenyl | 4-fluorophenyl | 4-ethoxyphenyl | |
| 4-fluorophenyl | 4-fluorophenyl | 4-phenylphenyl | |

EXAMPLE 10

Preparation of 1,1,1,3,4-pentachloro-3-methyl-1,3-disilabutane

A stirrer was added to a 250 ml, round bottomed flask, which was equipped with a bubbling column linked to a dry ice/aceton condenser and a chlorine gas cylinder. To the flask were added 100 g (0.41 mole) of 1,1,1,3-tetrachloro-3-methyl-1,3-disilabutane and 1 g of a reaction initiator, azobisisobutyronitrile, using carbon tetrachloride as a solvent. The obtained mixture was photoreacted for 5 hrs using a sun lamp, while bubbling chlorine gas and refluxing carbon tetrachloride. After confirming the degree of the reaction process by gas chromatography, the reaction mixture was distilled under vacuum to obtain 38 g of 1,1,1,3,4-pentachloro-3-methyl-1,3-disilabutane.

EXAMPLE 11

Preparation of 4-(chloromethyl)-6,6-bis(4-fluorophenyl)-4-methyl-4,6-disila-1,8-nonadiene To a 250 ml, three neck, round bottomed flask equipped with a condenser and a dropping funnel were added 8.5 g (31 mmol) of 1,1,1,3,4-pentachloro-3-methyl-1,3-disilabutane and 20 ml of tetrahydrofuran. Then, 31 ml of 4-fluorophenyl Grignard solution (2M solution in ether) was added thereto through the dropping funnel and was stirred at 40° C. for 3 hrs. 35 ml of allyl Grignard solution (2M solution in THF) was further added to be stirred for 2 hrs.

After adding the saturated aqueous NH₄Cl and stirring for 3 minutes, the obtained mixture was transferred to the dropping funnel, and the organic layer was separated to extract the aqueous layer three times with 30 ml of ether. The extrudate was pooled with the organic layer. After drying the mixture on the anhydrous MgSO₄ and filtering, the solvent was removed to obtain 13 g of the reaction product. If was confirmed by NMR analysis to be produced 4-(chloromethyl)-6,6-bis(4-fluorophenyl)-4-methyl-4,6-disila-1,8-nonadiene.

EXAMPLE 12

Preparation of 4-chloromethyl-6-(4-fluorophenyl)-4-methyl-6-(2-propenyl)-4,6-disila-1,8-nonadiene and 4-chloromethyl-4-methyl-6,6-bis(2-propenyl)-4,6-disila-1,8-nonadiene 5.7 g (20 mmol) of 1,1,1,3,4-pentachloro-3-methyl-1,3-disilabutane, 10 ml of 4-fluorophenyl Grignard solution (2M solution in ether) and 35 ml of allyl Grignard solution (2M solution is THF) were reacted in the same method as Example 11. 7.2 g of the mixture of the reaction products was obtained, which was confirmed by NMR analysis to be produced 4-chloromethyl-6-(4-fluorophenyl)-4-methyl-6-(2-propenyl)-4,6-disila-1,8-nonadiene and 4-chloromethyl-4-methyl-6,6-bis(2-propenyl)-4,6-disila-1,8-nonadiene.

EXAMPLE 13

Preparation of 7-chloro-4,4,6-tris(4-fluorophenyl)-6-methyl-4,6-disila-1-heptene In the name method as Example 11 were reacted 5.0 g (18 mmol) of 1,1,1,3,4-pentachloro-3-methyl-1,3-disilabutane, 27 ml of 4-fluorophenyl Grignard solution (2M solution in ether) and allyl Grignard solution to obtain 9.2 g of the mixture of the reaction products, which was confirmed by NMR analysis to be produced 7-chloro-4,4,6-tris(4-fluorophenyl)-6-methyl-4,6-disila-1-heptene.

EXAMPLE 14

Preparation of 4-chloromethyl-6-(4-fluorophenyl)-4-methyl-6-phenyl-4,6-disila-1,8-nonadiene To a 250 ml, three neck, round bottomed flask was equipped with a condenser and a dropping funnel were added 5.7 g (21 mmol) of 1,1,1,3,4-pentachloro-3-methyl-1,3-disilabutane and 25 ml of tetrahydrofuran. 10.5 ml of 4-fluorophenyl Grignard solution (2M in ether) was further added therein through the dropping funnel, and the mixture was stirred at 45° C. for 1 hr and 30 minutes. After adding 10.5 ml of phenyl Grignard solution (2M solution in THF) through the dropping funnel and stirring the mixture under reflux for 3 hrs, 23 ml of allyl Grignard solution (2M solution in THF) was added and the mixture was stirred for 2 hrs. In the same method as Example 1 were treated the reaction products to obtain 9 g of the mixture of the reaction products, which was confirmed by NMR analysis to be produced 4-chloromethyl-6-(4-fluorophenyl)-4-methyl-6-phenyl-4,6-disila-1,8-nonadiene.

EXAMPLE 15

Preparation of 4-chloromethyl-4-methyl-6-(4-phenylphenyl)-6-phenyl-4,6-disila-1,8-nonadiene To a 100 ml, three neck, round bottomed flask equipped with a condenser and a dropping funnel were added 0.4 g (17 mmol) of magnesium pieces and 25 ml of tetrahydrofuran. Then, 4 drops of the solution of 4.0 g (17 mmol) 4-bromobiphenyl in tetrahydrofuran were added therein through the dropping funnel, and the reaction was initiated. 4-bromobiphenyl solution was dropwise added, while maintaining the reaction temperature at 30° to 45° C. While adding the above prepared 4-phenylphenyl Grignard solution, 8.5 ml of phenyl Grignard solution (2M solution in THF) and 18 ml of allyl Grignard solution (2M solution in THF) to 1,1,1,3,4-pentachloro-3-methyl-1,3-disilabutane (17 mmol) in turn, the mixture was reacted in the same method as Example 11. 3.6 g of 4-chloromethyl-4-methyl-6-(4-phenylphenyl)-6-phenyl-4,6-disila-1,8-nonadiene mixed with the other products was obtained, using silica gel column (eluent: hexane).

EXAMPLE 16

Preparation of 4-chloromethyl-6,6-bis(4-ethoxyphenyl)-4-methyl-4,6-disila-1,8-nonadiene 6.4 g (23 mmol) of 1,1,1,3,4-pentachloro-3-methyl-1,3-disilabutane, 4-ethoxyphenyl Grignard solution as synthesized by the same method as Example 15 (6.6 ml of 4-bromophenetole, 1.1 g of magnesium pieces (46 mmol)) and 23 ml of allyl Grignard solution (2M solution in THF) were reacted in the same method as Example 11 to obtain 11.2 g of the mixture of the reaction products, which was confirmed by NMR analysis to be produced 4-chloromethyl-6,6-bis(4-ethoxyphenyl)-4-methyl-4,6-disila-1,8-nonadiene.

The compounds according to the procedure described in Examples 10 through 16 are listed in Table 3.

EXAMPLE 17

Preparation of 1,1,1,3,3,4-hexachloro-1,3-disilabutane 120 g (0.46 mole) of 1,1,1,3,3-pentachloro-1,3-disilabutane and 1.2 g of a reaction initiator, AIBN in carbon tetrachloride as solvent were reacted in the same apparatus as Example 10. The obtained reactant was photoreacted for 12 hrs using sun lamp, while bubbling chlorine gas and refluxing carbon tetrachloride. The produced reaction mixture was distilled under vacuum to obtain 32 g of 1,1,1,3,3,4-hexachloro-1,3-disilabutane.

EXAMPLE 18

Preparation of 4-chloromethyl-6-phenyl-4,6-bis(2-propenyl)-4,6-disila-1,8-nonadiene To a 250 ml, three neck, round bottomed flask equipped with a condenser and a dropping funnel was added 7.4 g (25 mmol) of 1,1,1,3,3,4-hexachloro-1,3-disilabutane and then, diluted with 30 ml of dry tetrahydrofuran. 12.5 ml of phenyl Grignard solution (2M solution in THF) was added at the room temperature for 1 hr through the dropping funnel, and the mixture was stirred for 1 hr and 30 minutes. 52 ml of allyl Grignard solution (2M solution in THF) was further dropwise added to the flask through the dropping funnel, and the mixture was reacted for 2 hrs. The reactant was treated in the same method as Example 1 to obtain 8 g of the

TABLE 3

$$\begin{array}{c} R_2 \quad\ CH_3 \\ |\quad\ \ \ | \\ R_3-Si-CH_2-Si-CH_2Cl \\ |\quad\ \ \ | \\ R_4 \quad\ R_1 \end{array}$$

| $R_1$ | $R_2$ | $R_3$ | $R_4$ | Example No. |
|---|---|---|---|---|
| chloro | chloro | chloro | chloro | 10 |
| 2-propenyl | 2-propenyl | 2-propenyl | 2-propenyl | |
| 2-propenyl | 2-propenyl | 4-fluorophenyl | 2-propenyl | 12 |
| 2-propenyl | 2-propenyl | 4-phenylphenyl | 2-propenyl | |
| 2-propenyl | 2-propenyl | phenyl | phenyl | |
| 2-propenyl | 2-propenyl | 4-ethoxyphenyl | phenyl | |
| 2-propenyl | 2-propenyl | 2-propenyl | phenyl | |
| 2-propenyl | 2-propenyl | 4-fluorophenyl | phenyl | 14 |
| 2-propenyl | 2-propenyl | 4-fluorophenyl | 4-fluorophenyl | 11 |
| 2-propenyl | 2-propenyl | 4-ethoxyphenyl | phenyl | 15 |
| 2-propenyl | 2-propenyl | 4-phenylphenyl | phenyl | |
| 2-propenyl | 2-propenyl | phenyl | phenyl | |
| 2-propenyl | 2-propenyl | 2-propenyl | 4-ethoxyphenyl | |
| 2-propenyl | 2-propenyl | 4-ethoxyphenyl | 4-ethoxyphenyl | 16 |
| 2-propenyl | 2-propenyl | 4-phenylphenyl | 4-ethoxyphenyl | |
| 2-propenyl | 2-propenyl | 4-phenylphenyl | 4-phenylphenyl | |
| 2-propenyl | 2-propenyl | phenyl | 4-phenylphenyl | |
| 4-ethoxyphenyl | 2-propenyl | phenyl | phenyl | |
| 4-ethoxyphenyl | 2-propenyl | 4-phenylphenyl | phenyl | |
| 4-ethoxyphenyl | 2-propenyl | 4-fluorophenyl | 4-fluorophenyl | |
| 4-ethoxyphenyl | 2-propenyl | 4-ethoxyphenyl | 4-fluorophenyl | |
| 4-ethoxyphenyl | 2-propenyl | 4-phenylphenyl | 4-fluorophenyl | |
| 4-ethoxyphenyl | 2-propenyl | phenyl | 4-fluorophenyl | |
| 4-ethoxyphenyl | 2-propenyl | 4-ethoxyphenyl | 4-ethoxyphenyl | |
| 4-ethoxyphenyl | 2-propenyl | 4-phenylphenyl | 4-ethoxyphenyl | |
| 4-ethoxyphenyl | 2-propenyl | phenyl | 4-ethoxyphenyl | |
| 4-ethoxyphenyl | 2-propenyl | 4-phenylphenyl | 4-phenylphenyl | |
| 4-fluorophenyl | 2-propenyl | 4-fluorophenyl | 4-fluorophenyl | 13 |
| 4-fluorophenyl | 2-propenyl | 4-ethoxyphenyl | 4-fluorophenyl | |
| 4-fluorophenyl | 2-propenyl | phenyl | 4-fluorophenyl | |
| 4-fluorophenyl | 2-propenyl | 4-phenylphenyl | 4-fluorophenyl | |
| 4-fluorophenyl | 2-propenyl | 4-ethoxyphenyl | 4-ethoxyphenyl | |
| 4-fluorophenyl | 2-propenyl | phenyl | 4-ethoxyphenyl | |
| 4-fluorophenyl | 2-propenyl | phenyl | phenyl | |
| 4-fluorophenyl | 2-propenyl | 4-phenylphenyl | phenyl | |
| 4-fluorophenyl | 2-propenyl | 4-phenylphenyl | 4-phenylphenyl | |
| 4-fluorophenyl | 2-propenyl | 4-ethoxyphenyl | 4-phenylphenyl | | mixture of the reaction products, which was confirmed by NMR analysis to be produced 4-chloromethyl-6-phenyl-4,6-bis(2-propenyl)-4,6-disila-1,8-nonadiene.

EXAMPLE 19

Preparation of
4-chloromethyl-6-(4-fluorophenyl)-6-(4-phenylphenyl)-4-(2-propenyl)-4,6-disila-1,8-nonadiene.

To the flask equipped with the same apparatus as Example 18 were added 6.5 g (22 mole) of 1,1,1,3,3,4-hexachloro-1,3-disilabutane and 25 ml of dry tetrahydrofuran and further added 11 ml of 4-fluorophenyl Grignard solution (2M solution in ether) at the room temperature through the dropping funnel, and the obtained mixture was stirred for 1 hr. After reacting 4-phenylphenyl Grignard solution (22 mmol, 5.2 g of 4-bromobiphenyl, 1.0 g of magnesium pieces and 0.4 g of iodine) as prepared in the same method as Example 15 under reflux, 35 ml of allyl Grignard solution (2M in THF) was added therein and stirred for 2 hrs.

In the same method as Example 1 was treated the reactant to obtain 13.2 g of the mixture of the reaction products, which was confirmed by NMR analysis to be produced 4-chloromethyl-6-(4-fluorophenyl)-6-(4-phenylphenyl)-4-(2-propenyl)-4,6-disila-1,8-nonadiene.

EXAMPLE 20

Preparation of
4-chloromethyl-4,6-bis(4-ethoxyphenyl)-6-(4-fluorophenyl)-4,6-disila-1,8-nonadiene In the same apparatus and procedures as Example 18 were reacted 5.9 g (20 mmol) of 1,1,1,3,3,4-hexachloro-1,3-disilabutane and 10 ml of 4-fluorophenyl Grignard solution (2M solution in ether). 4-ethoxyphenyl Grignard solution (40 mmol, 5.7 ml of 4-bromophenetole, 1.5 g of magnesium pieces and 0.5 g of iodine) as synthesized in the same method as Example 15 was added therein and the obtained mixture was reacted under reflux for 4 hrs. Then, 22 ml of allyl Grignard solution (2M in THF) was added and stirred for 2 hrs. The reactant was treated in the same method as Example 1 to obtain 15.3 g of the mixture of the reaction products, which was confirmed by NMR analysis to be produced 4-chloromethyl-4,6-bis(4-ethoxyphenyl)-6-(4-fluorophenyl)-4,6-disila-1,8-nonadiene.

EXAMPLE 21

Preparation of
7-chloro-4,4,6,6-tetraphenyl-4,6-disila-1-heptene

To the flask of the same apparatus as Example 18 were added 5.9 g (20 mmol) of 1,1,1,3,3,4-hexachloro-1,3-disilabutane and 40 ml of phenyl Grignard solution (2M in THF) and the obtained mixture was stirred and reacted at 45° C. for 5 hrs. After completing the reaction, the temperature was reduced to the room temperature. 12 ml of allyl Grignard solution (2M in THF) was added therein, and then stirred for 2 hrs. In the same method as Example 1 was treated the reactants to obtain 17.2 g of the mixture of the reaction products, which was confirmed by NMR analysis to be produced 7-chloro-4,4,6,6-tetraphenyl-4,6-disila-1-heptene.

EXAMPLE 22

Preparation of
4-chloromethyl-6,6-bis(4-fluorophenyl)-4-phenyl-4,6-disila-1,8-nonadiene 6.5 g (22 mmole) of 1,1,1,3,3,4-hexachloro-1,3-disilabutane and 22 ml of fluorophenyl Grignard solution (2M in ether) were reacted in the flask having the same apparatus as Example 18 under reflux for 4 hrs. 11 ml of phenyl Grignard solution (2M in THF) was added therein, after reducting the temperature to the room temperature. The mixture was stirred for 1 hr and reacted under reflux for 1 hr. 23 ml of allyl Grignard solution (2M in THF) was added therein and stirred for 2 hrs, after reducing again the temperature to the room temperature. In the same method as Example 1 was treated the reactants to obtain 13.7 g of the mixture of the reaction products, which was confirmed by NMR analysis to be produced 4-chloromethyl-6,6-bis(4-fluorophenyl)-4-phenyl-4,6-disila-1,8-nonadiene.

EXAMPLE 23

Preparation of
7-chloro-4,6,6-tris(4-ethoxyphenyl)-4-(4-biphenyl)-4,6-disila-1-heptene To the flask having the same apparatus as Example 18 were added 5.9 g (20 mmole) of 1,1,1,3,3,4-hexachloro-1,3-disilabutane and 20 ml of dry tetrahydrofuran. Then, 4-phenylphenyl Grignard solution (20 mmole, 4.7 g of 4-bromobiphenyl, 2.4 g of magnesium pieces and 0.7 g of iodine) as synthesized in the same method as Example 15 was dropwise added through the dropping funnel and the mixture was stirred for 2 hrs. Continuously, the synthesized 4-ethoxyphenyl Grignard solution (60 mmol, 8.6 ml of 4-bromophenetole, 2.4 g of magnesium pieces and 0.7 g of iodine) was added therein and the mixture was reacted at 45° C. for 5 hrs. 11 ml of allyl Grignard solution (2M in THF) was added and stirred for 2 hrs, after reducing the temperature to the room temperature. In the same method as Example 1 was treated the reactants to obtain 16.2 g of the mixture of the reaction products, which was confirmed by NMR analysis to be produced 7-chloro-4,6,6-tris(4-ethoxyphenyl)-4-(4-biphenyl)-4,6-disila-1-heptene.

The compounds prepared according to the procedure described in Examples 18 through 23 are listed in Table 4.

TABLE 4

$$R_4-\underset{\underset{R_5}{|}}{\overset{\overset{R_3}{|}}{Si}}-CH_2-\underset{\underset{R_2}{|}}{\overset{\overset{R_1}{|}}{Si}}-CH_2Cl \quad (17)$$

| $R_1$ | $R_2$ | $R_3$ | $R_4$ | $R_5$ |
|---|---|---|---|---|
| chloro | chloro | chloro | chloro | chloro |
| 2-propenyl | 2-propenyl | 2-propenyl | 4-ethoxyphenyl | 4-ethoxyphenyl |
| 2-propenyl | 2-propenyl | 2-propenyl | 4-phenylphenyl | 4-ethoxyphenyl |
| 2-propenyl | 2-propenyl | 2-propenyl | phenyl | 4-ethoxyphenyl |
| 2-propenyl | 2-propenyl | 2-propenyl | phenyl | phenyl |
| 2-propenyl | 2-propenyl | 2-propenyl | 4-fluorophenyl | phenyl |

TABLE 4-continued $$R_4-\underset{\underset{R_5}{|}}{\overset{\overset{R_3}{|}}{Si}}-CH_2-\underset{\underset{R_2}{|}}{\overset{\overset{R_1}{|}}{Si}}-CH_2Cl$$

| R₁ | R₂ | R₃ | R₄ | R₅ | |
|---|---|---|---|---|---|
| 2-propenyl | 2-propenyl | 2-propenyl | 4-phenylphenyl | phenyl | |
| 2-propenyl | 2-propenyl | 2-propenyl | 4-fluorophenyl | 4-fluorophenyl | |
| 2-propenyl | 2-propenyl | 2-propenyl | 4-ethoxyphenyl | 4-fluorophenyl | |
| 2-propenyl | 2-propenyl | 2-propenyl | phenyl | 2-propenyl | (18) |
| 2-propenyl | 2-propenyl | 2-propenyl | 4-fluorophenyl | 2-propenyl | |
| 2-propenyl | 2-propenyl | 2-propenyl | 4-ethoxyphenyl | 2-propenyl | |
| 2-propenyl | 2-propenyl | 2-propenyl | 4-phenylphenyl | 2-propenyl | |
| 2-propenyl | 2-propenyl | 2-propenyl | 4-fluorophenyl | 4-phenylphenyl | (19) |
| 4-fluorophenyl | 4-fluorophenyl | 2-propenyl | phenyl | phenyl | |
| 4-fluorophenyl | 4-fluorophenyl | 2-propenyl | 4-ethoxyphenyl | phenyl | |
| 4-fluorophenyl | 4-fluorophenyl | 2-propenyl | 4-phenylphenyl | phenyl | |
| 4-fluorophenyl | 4-fluorophenyl | 2-propenyl | 4-fluorophenyl | phenyl | |
| 4-fluorophenyl | 4-fluorophenyl | 2-propenyl | 4-ethoxyphenyl | 4-ethoxyphenyl | |
| 4-fluorophenyl | 4-fluorophenyl | 2-propenyl | 4-phenylphenyl | 4-ethoxyphenyl | |
| 4-fluorophenyl | 4-fluorophenyl | 2-propenyl | 4-fluorophenyl | 4-ethoxyphenyl | |
| 4-fluorophenyl | 4-fluorophenyl | 2-propenyl | 4-fluorophenyl | 4-flurorphenyl | |
| 4-fluorophenyl | 4-fluorophenyl | 2-propenyl | 4-phenylphenyl | 4-flurorphenyl | |
| 2-propenyl | 4-ethoxyphenyl | 2-propenyl | phenyl | phenyl | |
| 2-propenyl | 4-ethoxyphenyl | 2-propenyl | 4-phenylphenyl | phenyl | |
| 2-propenyl | 4-ethoxyphenyl | 2-propenyl | 4-fluorophenyl | 4-flurorphenyl | |
| 2-propenyl | 4-ethoxyphenyl | 2-propenyl | 4-phenylphenyl | 4-fluorophenyl | |
| 2-propenyl | 4-ethoxyphenyl | 2-propenyl | phenyl | 4-fluorophenyl | |
| 2-propenyl | 4-ethoxyphenyl | 2-propenyl | 4-ethoxyphenyl | 4-ethoxyphenyl | |
| 2-propenyl | 4-ethoxyphenyl | 2-propenyl | 4-phenylphenyl | 4-ethoxyphenyl | |
| 2-propenyl | 4-ethoxyphenyl | 2-propenyl | 4-fluorophenyl | 4-ethoxyphenyl | (20) |
| 2-propenyl | 4-ethoxyphenyl | 2-propenyl | phenyl | 4-ethoxyphenyl | |
| 4-ethoxyphenyl | 4-ethoxyphenyl | 2-propenyl | phenyl | phenyl | |
| 4-ethoxyphenyl | 4-ethoxyphenyl | 2-propenyl | 4-fluorophenyl | phenyl | |
| 4-ethoxyphenyl | 4-ethoxyphenyl | 2-propenyl | 4-ethoxyphenyl | 4-phenylphenyl | (23) |
| 4-ethoxyphenyl | 4-ethoxyphenyl | 2-propenyl | 4-phenylphenyl | 4-fluorophenyl | |
| 4-ethoxyphenyl | 4-ethoxyphenyl | 2-propenyl | 4-ethoxyphenyl | 4-fluorophenyl | |
| 4-ethoxyphenyl | 4-ethoxyphenyl | 2-propenyl | 4-ethoxyphenyl | 4-ethoxyphenyl | |
| 2-propenyl | phenyl | 2-propenyl | 4-fluorophenyl | 4-fluorophenyl | (22) |
| 2-propenyl | 4-fluorophenyl | 2-propenyl | 4-fluorophenyl | 4-fluorophenyl | |
| 2-propenyl | 4-fluorophenyl | 2-propenyl | 4-phenylphenyl | phenyl | |
| 2-propenyl | 4-fluorophenyl | 2-propenyl | 4-ethoxyphenyl | 4-ethoxyphenyl | |
| 2-propenyl | 4-fluorophenyl | 2-propenyl | 4-fluorophenyl | 4-ethoxyphenyl | |
| 2-propenyl | 4-fluorophenyl | 2-propenyl | phenyl | 4-ethoxyphenyl | |
| 2-propenyl | 4-fluorophenyl | 2-propenyl | 4-phenylphenyl | 4-ethoxyphenyl | |
| 2-propenyl | 4-fluorophenyl | 2-propenyl | 4-fluorophenyl | 4-phenylphenyl | |
| 4-fluorophenyl | 4-ethoxyphenyl | 2-propenyl | 4-ethoxyphenyl | 4-ethoxyphenyl | |
| 4-fluorophenyl | 4-ethoxyphenyl | 2-propenyl | 4-phenylphenyl | 4-ethoxyphenyl | |
| phenyl | phenyl | 2-propenyl | phenyl | phenyl | (21) |
| 4-fluorophenyl | 4-ethoxyphenyl | 2-propenyl | 4-phenylphenyl | phenyl | |
| 4-fluorophenyl | 4-ethoxyphenyl | 2-propenyl | 4-fluorophenyl | 4-fluorophenyl | |
| 4-fluorophenyl | 4-ethoxyphenyl | 2-propenyl | 4-ethoxyphenyl | 4-fluorophenyl | |
| 4-fluorophenyl | 4-ethoxyphenyl | 2-propenyl | 4-fluorophenyl | 4-phenylphenyl | |

EXAMPLE 24

Preparation of 2-(4-methoxyphenyl)-2,4,4-trimethyl-2,4-disila-1-(1H-1,2,4-triazole-1-yl)pentane To a 100 ml, three neck, round bottomed flask equipped with a condenser and a dropping funnel were added 0.6 g of NaH (20 mmol, 80% dispersion in mineral oil) and 10 ml of dry DMF. After dissolving 1.4 g (20 mol) of 1,2,4-triazole dried under vacuum at the room temperature in 12 ml of dry DMF, the solution was added through the dropping funnel, and then the mixture was stirred for 30 minutes. 5.2 g (18 mmol) of 1-chloro-2-(4-methoxyphenyl)-2,4,4-trimethyl-2,4-disilapentane was diluted with 5 ml of dry DMF. The diluted solution was dropwise added to the flask, and then the mixture was stirred at 45° C. for 5 hrs. In the same method as Example 1 was treated the reactants and separated by silica gel column (eluent: hexane) to obtain 0.7 g of 2-(4-methoxyphenyl)-2,4,4-trimethyl-2,4-disila-1-(1H-1,2,4-triazole-1-yl)pentane.

$^1$H-NMR(CCl₄, δ): 0.4(s, 9H); 0.5(s, 3H); 0.6(s, 2H); 3.7(s, 2H); 7.0-7.7(m, 4H): 7.8(d, 2H).

EXAMPLE 25

Preparation of 2,4,4-trimethyl-2-(4-phenylphenyl)-2,4-disila-1-(1H-1,2,4-triazole-1-yl)pentane 0.7 g of NaH(23 mmol, 80% dispersion in mineral oil) was reacted with 1.6 g (23 mmol) of 1,2,4-triazole to obtain sodium triazole salts. The salts was reacted with 7.3 g (22 mmol) of 1-chloro-2,4,4-trimethyl-2-(4-phenylphenyl)-2,4-disilapentane at 45° C. for 4 hrs, and then the reactant was separated by silica gel column (eluent: ether) to obtain 0.8 g of 2,4,4-trimethyl-2-(4-phenylphenyl)-2,4-disila-1-(1H-1,2,4-triazole-1-yl)pentane.

$^1$H-NMR(CCl₄, δ): 0.3(s, 9H); 0.4(s, 3H); 0.5(s, 2H); 3.7(s, 2H); 7.5(s, 4H): 7.8(d, 2H).

EXAMPLE 26

Preparation of
2,4-bis(4-fluorophenyl)-2,4-dimethyl-2,4-disila-(1H-1,2,4-triazole-1-yl)pentane A 50 ml, round bottomed flask was equipped with a condenser and a magnetic stirrer. 7.5 g (50 mmol) of NaI was added therein and dissolved with 30 ml of acetone. 15.1 g of the mixture of the reaction products containing 1-chloro-2,4-bis(4-fluorophenyl)-2,4-dimethyl-2,4-disilapentane was added, and then the mixture was reacted under reflux for 4 hrs and 30 minutes. After filtering the produced NaCl off and evaporating to remove acetone, the residue was treated with water to resolve the excess of NaI, and then the organic material was extracted two times with 20 ml of ether. The extract was dried on anhydrous $MgSO_4$, and filtered to remove the solvent. After confirming by NMR analysis that the halogen exchange reaction was completely carried out, the following reaction was directly carried out without any purification.

To a 100 ml, round bottomed flask equipped with a condenser and a dropping funnel were added 0.5 g of NaH (17 mmol, 80% dispersion in mineral oil) and 7 ml of dry DMF. After resolving 1.2 g (17 mmol) of 1,2,4-triazole which was dried under vacuum at the room temperature in 10 ml of dry DMF, the solution was added through the dropping funnel and the mixture was stirred for 20 minutes. 16.5 g of the mixture of the reaction products containing 2,4-bis(4-fluorophenyl)-1-iodo-2,4-dimethyl-2,4-disilapentane as previously prepared was diluted with 10 ml of dry DMF to be dropwisely added to the flask, and the mixture was stirred at 45° C. for 4 hrs. After confirming by GC that all reactants were participated with the reaction, the aqueous saturated $NH_4Cl$ solution was added therein, and the organic material was extracted three times with 30 ml of ether. The extract was dried on anhydrous $MgSO_4$, and filtered to remove the solvent. The residue was separated by silica gel column (eluent: ether) to obtain 1.4 g of 2,4,-bis(4-fluorophenyl)-2,4-dimethyl-2,4-disila-(1H-1,2,4-triazole-1-yl)pentane.

$^1$H-NMR($CCl_4$, δ): 0.2(s, 6H); 0.3(s, 3H); 0.4(s, 2H); 3.7(s, 2H); 7.2(m, 8H); 7.7(d, 2H).

EXAMPLE 27

Preparation of
4-(4-fluorobenzyl)-2-(4-fluorophenyl)-2,4-dimethyl-2,4-disila-1-(1H-1,2,4-triazole-1-yl)petane 2.4 g (16 mmol) of NaI and 5.9 g (16 mmol) of 1-chloro-4-(4-fluorobenzyl)-2-(4-fluorophenyl)-2,4-dimethyl-2,4-disilapentane were reacted in the same method as Example 26 to carry out the halogen exchange reaction.

In the same method as Example 26 were reacted 0.5 g (17 mmol) of NaH and 1.2 g (17 mmol) of 1,2,4-triazole to obtain the sodium triazole salt. The salt was reacted with 6.2 g (13 mmol) of 4-(4-fluorobenzyl)-2-(4-fluorophenyl)-1-iodo-2,4-dimethyl-2,4-disilapentane as above prepared at 45° C. for 4 hrs, and then the reactant was treated. The obtained reactent was separated by silica gel column (eluent: ether) to obtain 2.4 g of 4-(4-fluorobenzyl)-2-(4-fluorophenyl)-2,4-dimethyl-2,4-disila-1-(1H-1,2,4-triazole-1-yl)petane.

$^1$H-NMR($CCl_4$, δ): −0.2(s, 3H); −0.1(s, 3H); 0.2(s, 2H); 0.4(s, 3H); 2.0(s, 2H); 3.8(s, 2H); 7.2(m, 8H); 7.8(d, 2H).

EXAMPLE 28

Preparation of
4-(4-ethoxyphenyl)-2-(4-fluorophenyl)-2,4-dimethyl-2,4-disila-1-(1H-1,2,4-triazole-1-yl)pentane In the same as Example 26 were reacted 2.2 g (15 mmol) of NaI and 27 g of the mixture of the reaction products containing 1-chloro-4-(4-ethoxyphenyl)-2-(4-fluorophenyl)-2,4-dimethyl-2,4-disilapentane to carry out the halogen exchange reaction.

In the same method as Example 26 were reacted 0.4 g (13 mmol) of NaH and 0.9 g (13 mmol) of 1,2,4-triazole to obtain the sodium triazole salt. The salt was reacted with 27 g of the mixture containing 4-(4-ethoxyphenyl)-2-(4-fluorophenyl)-1-iodo-2,4-dimethyl-2,4-disilapentane as previously prepared at 45° C. for 5 hrs, and then the reactant was treated. The obtained reactant was separated by silica gel column (eluent: ether) to obtain 1.3 g of 4-(4-ethoxyphenyl)-2-(4-fluorophenyl)-2,4-dimethyl-2,4-disila-1-(1H-1,2,4-triazole-1-yl)pentane.

$^1$H-NMR($CCl_4$, δ): 0.2(s, 6H); 0.3(s, 3H); 1.4(t, 3H); 3.7(s, 2H); 4.0(s, 4H); 7.1(m, 8H); 7.6(d, 2H).

EXAMPLE 29

Preparation of
4-(4-chlorophenyl)-2-(4-fluorophenyl)-2,4-dimethyl-2,4-disila-1-(1H-1,2,4-triazole-1-yl)pentane In the same method as Example 26 were reacted 3.7 g (25 mmol) of NaI and 23 g of the compounds containing 1-chloro-4-(4-chlorophenyl)-2-(4-fluorophenyl)-2,4-dimethyl-2,4-disilapentane to carry out the halogen exchange reaction.

In the same method as Example 26 were reacted 0.6 g (20 mmol) of NaH and 1.4 g (20 mmol) of 1,2,4-triazole to obtain the sodium triazole salt. The salt was reacted with 25.8 g of the mixture containing 4-(4-chlorophenyl)-2-(4-fluorophenyl)-1-iodo-2,4-dimethyl-2,4-disilapentane as previously prepared at 45° C. for 5 hrs, and then the reactant was treated. The obtained reactant was separated by silica gel column (eluent: ether) to obtain 4.5 g of 4-(4-chlorophenyl)-2-(4-fluorophenyl)-2,4-dimethyl-2,4-disila-1-(1H-1,2,4-triazole-1-yl)pentane.

$^1$H-NMR($CCl_4$, δ): 0.2(broad s, 6H); 0.3(s, 2H); 0.4(s, 2H); 3.7(s, 2H); 7.2(m, 4H); 7.3(s, 4H); 7.6(d, 2H).

EXAMPLE 30

Preparation of
2,2-bis(4-chlorophenyl)-4,4-dimethyl-2,4-disila-1-(1H-1,2,4-triazole-1-yl)pentane In the same method as Example 26 were reacted 3.0 g (20 mmol) of NaI and 18.3 g of the compound containing 1-chloro-2,2-bis(4-chlorophenyl)-4,4-dimethyl-2,4-disilapentane to carry out the halogen exchange reaction.

In the same method as Example 26 were reacted 0.5 g (17 mmol) of NaH and 1.2 g (17 mmol) of 1,2,4-triazole to obtain the sodium triazole salt. The salt was reacted with 17.0 g of the mixture containing 2,2-bis(4-chlorophenyl)-1-iodo-4,4-dimethyl-2,4-disilapentane as previously prepared at 45° C. for 4 hrs. The reactant was separated by silica gel column (eluent: ether) to obtain 3.6 g of 2,2-bis(4-chlorophenyl)-4,4-dimethyl-2,4-disila-1-(1H-1,2,4-triazole-1-yl)pentane.

$^1$H-NMR($CCl_4$, δ): 0.0(s, 9H); 0.3(s, 2H); 4.3(s, 2H); 7.3(s, 8H); 7.8(d, 2H)

EXAMPLE 31

Preparation of 2,2-bis(4-ethoxyphenyl)-4-(4-fluorophenyl)-4-methyl-2,4-disila-1-(1H-1,2,4-triazole-1-yl)pentane In the same method as Example 26 were reacted 2.4 g (16 mmol) of NaI and 16.7 g of the compound containing 1-chloro-2,2-bis(4-ethoxyphenyl)-4-(4-fluorophenyl)-4-methyl-2,4-disilapentane to carry out the halogen exchange reaction.

In the same method as Example 26 were reacted 0.4 g (13 mmol) of NaH and 0.9 g (13 mmol) of 1,2,4-triazole to obtain the sodium triazole salt. The salt was reacted with 15.8 g of the mixture containing 2,2-bis(4-ethoxyphenyl)-4-(4-fluorophenyl)-1-iodo-4-methyl-2,4-disilapentane as previously prepared at 50° C. for 4 hrs and 30 minutes. The reactant was separated by silica gel column (eluent: ether) to obtain 2.8 g of 2,2-bis(4-ethoxyphenyl)-4-(4-fluorophenyl)-4-methyl-2,4-disila-1-(1H-1,2,4-triazole-1-yl)pentane.

$^1$H-NMR(CCl$_4$, $\delta$): 0.2(s, 6H); 0.4(s, 2H); 4.2(s, 2H); 6.7–7.4 (m, 12H); 7.6(d, 2H).

EXAMPLE 32

Preparation of 4-(4-chlorophenyl)-2-(4-ethoxyphenyl)-2-(4-methoxyphenyl)-4-methyl-2,4-disila-1-(1H-1,2,4-triazole-1-yl)pentane In the same method as Example 26 were reacted 2.7 g (18 mmol) of NaI and 19.2 g of the compound 1-chloro-4-(4-chlorophenyl)-2-(4-ethoxyphenyl)-2-(4-methoxyphenyl)-2,4-disilapentane to carry out the halogen exchange reaction.

In the same method as Example 26 were reacted 0.4 g (15 mmol) of NaH and 1.0 g (15 mmol) of 1,2,4-triazole to obtain the sodium triazole salt. The salt was reacted with 17.5 g of the mixture containing 4-(4-chlorophenyl)-2-(4-ethoxyphenyl)-1-iodo-2-4-methoxyphenyl-4-methyl-2,4-disilapentane as previously prepared at 45° C. for 4 hrs. The reactants were separated by silica gel column (eluent: ether) to obtain 2.2 g of 4-(4-chlorophenyl)-2-(4-ethoxyphenyl)-2-(4-methoxyphenyl)-4-methyl-2,4-disila-1-(1H-1,2,4-triazole-1-yl)pentane.

$^1$H-NMR(CCl$_4$, $\delta$): 0.2(s, 6H); 0.5(s, 2H); 4.2(s, 2H); 6.9–7.6(m, 12H): 7.7(d, 2H).

EXAMPLE 33

Preparation of 4-(4-chlorophenyl)-2,2-bis(4-fluorophenyl)-4-methyl-2,4-disila-1-(1H-1,2,4-triazole-1-yl)pentane In the same method as Example 26 were reacted 3.1 g (21 mmol) of NaI and 21.3 g of the compound 1-chloro-4-(4-chlorophenyl)-2,2-bis(4-fluorophenyl)-4-methyl-2,4-disilapentane to carry out the halogen exchange reaction.

In the same method as Example 26 were reacted 0.5 g (17 mmol) of NaH and 18.7 g of the mixture containing 4-(4-chlorophenyl)-2,2-bis(4-fluorophenyl)-1-iodo-4-methyl-2,4-disilapentane as previously prepared for 5 hrs. The reactants were separated by silica gel column (eluent: ether) to 2.1 g of 4-(4-chlorophenyl)-2,2-bis(4-fluorophenyl)-4-methyl-2,4-disila-1-(1H-1,2,4-triazole-1-yl)pentane.

$^1$H-NMR(CCl$_4$, $\delta$): 0.2(s, 6H); 0.5(s, 2H); 4.1(s, 2H); 7.0–7.6(m, 12H): 7.8(d, 2H).

Example 34

Preparation of 4,4,6-tris(4-fluorophenyl)-6-methyl-4,6-disila-7-(1H-1,2,4-triazole-1-yl)-1-heptane In the same method as Example 26 were reacted 4.5 g (30 mmol) of NaI and 9.2 g of the mixture of the reaction products containing 7-chloro-4,4,6-tris(4-fluorophenyl)-6-methyl-2,6-disilaheptane to carry out the halogen exchange reaction.

In the same method as Example 26 were reacted 0.6 g (20 mmol) of NaH and 1.4 g (20 mmol) of 1,2,4-triazole to obtain the sodium triazole salt. The salt was reacted with 8.3 g of 4,4,6-tris(4-fluorophenyl)-7-iodo-6-methyl-2,6-disilaheptane as previously prepared at 45° C. for 4 hrs. The reactants were separated by silica gel column (eluent: ether) to obtain 2.2 g of 4,4,6-tris(4-fluorophenyl)-6-methyl-4,6-disila-7-(1H-1,2,4-triazole-1-yl)-1-heptane.

$^1$H-NMR(CCl$_4$, $\delta$): 0.2(s, 3H); 0.8(s, 2H); 1.9(d, 2H); 3.0(s, 2H); 4.6–5.0(m, 2H); 5.3–5.7(m, 1H); 6.8–7.6(m, 12H); 7.8(d, 2H).

EXAMPLE 35

Preparation of 6-(4-fluorophenyl)-4-methyl-6-phenyl-4,6-disila-4-(1H-1,2,4-triazole-1-ylmethyl)-1,8-nonadiene In the same method as Example 26 were reacted 3.5 g (23 mmol) of NaI and 9.0 g of the mixture of the reaction products containing 4-chloromethyl-6(4-fluorophenyl)-4-methyl-6-phenyl-4,6-disila-1,8-nonadiene to carry out the halogen exchange reaction.

In the same method as Example 26 were reacted 0.6 g (20 mmol) of NaH and 1.4 g (20 mmol) of 1,2,4-triazole to obtain the sodium triazole salt. The salt was reacted with 9.0 g of 6-(4-fluorophenyl)-4-iodomethyl-4-methyl-6-phenyl-4,6-disila-1,8-nonadiene as previously prepared at 45° C. for 5 hrs. The reactants were separated by silica gel column (eluent: ether) to obtain 9.0 g of 6-(4-fluorophenyl)-4-methyl-6-phenyl-4,6-disila-4-(1H-1,2,4-triazole-1-ylmethyl)-1,8-nonadiene.

$^1$H-NMR(CCl$_4$, $\delta$): 0.2(s, 3H); 0.4(s, 2H); 1.2–1.8(m, 4H); 3.6–3.7(m, 2H); 4.6–4.9(m, 4H): 5.3–6.0(m, 2H); 6.8–7.5(m, 1H)

EXAMPLE 36

Preparation of 4-methyl-6-(4-phenylphenyl)-6-phenyl-4,6-disila-4-(1H-1,2,4-triazole-1-ylmethyl)-1,8-nonadiene In the same method as Example 26 were reacted 1.9 g (13 mmol) of NaI and 3.6 g of the mixture of the reaction products containing 4-chloromethyl-4-methyl-6-(4-phenylphenyl)-6-phenyl-4,6-disila-1,8-nonadiene to carry out the halogen exchange reaction.

In the same method as Example 26 were reacted 0.3 g (10 mmol) of NaH and 3.0 g of 4-iodomethyl-4-methyl-6-(4-phenylphenyl)-6-phenyl-4,6-disila-1,8-nonadiene as previously prepared at 45° C. for 4 hrs. The reactants were separated by silica gel column (eluent: ether) to obtain 1.2 g of 4-methyl-6-(4-phenylphenyl)-6-phenyl-4,6-disila-4-(1H-1,2,4-triazole-1-ylmethyl)-1,8-nonadiene.

$^1$H-NMR(CCl$_4$, $\delta$): 0.1–0.4(s, 5H); 1.3–1.7(m, 4H); 3.6–3.7(m, 2H); 4.7–4.9(m, 4H): 5.3–6.0(m, 2H); 7.3–7.5(m, 16H)

EXAMPLE 37

Preparation of
6,6-bis(4-fluorophenyl)-4-(2-propenyl)-4,6-disila-4-(1H-1,2,4-triazole-1-ylmethyl)-1,8-nonadiene In the same method as Example 26 were reacted 2.5 g (17 mmol) of NaI and 9.2 g of the mixture of the reaction products containing 4-chloromethyl-6,6-bis(4-fluorophenyl)-4-(2-propenyl)-4,6-disila-1,8-nonadiene to carry out the halogen exchange reaction.

In the same method as Example 26 were reacted 0.5 g (15 mmol) and 1.0 g (15 mmol) of 1,2,4-triazole to obtain the sodium salt of triazole. The salt was reacted with 12.3 g of mixture of the reaction products containing 6,6-bis(4-fluorophenyl)-4-iodomethyl-4-(2-propenyl)-4,6-disila-1,8-nonadiene as previously prepared at 50° C. for 5 hrs. The reactant was separated by silica gel column (eluent: ether) to obtain 1.8 g of 6,6-bis(4-fluorophenyl)-4-(2-propenyl)-4,6-disila-4-(1H-1,2,4-triazole-1-ylmethyl)-1,8-nonadiene.

$^1$H-NMR(CCl$_4$, $\delta$): 0.8(s, 2H); 1.6–3.1(m, 6H); 3.6(s, 2H); 4.9–5.2(m, 6H); 5.5–6.2(m, 3H); 7.1–8.0(m, 10H)

EXAMPLE 38

Preparation of
6-(4-ethoxyphenyl)-6-(4-phenylphenyl)-4-(2-propenyl)-4,6-disila-4-(1H-1,2,4-triazole-1-ylmethyl)-1,8-nonadiene In the same method as Example 26 were reacted 2.2 g (15 mmol) of NaI and 10.7 g of the mixture of the reaction products containing 4-chloromethyl-6-(4-ethoxyphenyl)-6-(4-phenylphenyl)-4-(2-propenyl)-4,6-disila-1,8-nonadiene to carry out the halogen exchange reaction.

In the same method as Example 26 were reacted 0.4 g (12 mmol) of NaH and 0.8 g (12 mmol) of 1,2,4-triazole to obtain the sodium salt of triazole. The salt was reacted with 13.4 g of the mixture of the reaction products containing 6-(4-ethoxyphenyl)-4-iodomethyl-6-(4-phenylphenyl)-4-(2-propenyl)-4,6-disila-1,8-nonadiene as above prepared at 45° C. for 4 hrs and 30 minutes. The reactant was separated by silica gel column (eluent: ether) to obtain 2.7 g of 6-(4-ethoxyphenyl)-6-(4-phenylphenyl)-4-(2-propenyl)-4,6-disila-4-(1H-1,2,4-triazole-1-ylmethyl)-1,8-nonadiene.

$^1$H-NMR(CCl$_4$, $\delta$): 0.6(s, 2H); 1.5–3.0(m, 6H); 3.7(s, 2H); 4.9–5.1(m, 6H); 5.5–6.1(m, 3H); 6.9–7.9(m, 15H)

EXAMPLE 39

Preparation of
4,6,6-tris(4-fluorophenyl)-4,6-disila-4-(1H-1,2,4-triazole-1-ylmethyl)-1,8-nonadiene In the same method as Example 26 were reacted 2.4 g (16 mmol) of NaI and 9.2 g of the mixture of the reaction products containing 4-chloromethyl-4,6,6-tris(4-fluorophenyl)-4,6-disila-1,8-nonadiene to carry out the halogen exchange reaction.

In the same method as Example 26 were reacted 0.4 g (13 mmol) of NaH and 0.9 g (13 mmol) of 1,2,4-triazole to obtain the sodium salt of triazole. The salt was reacted with 13.1 g of the mixture containing 4,6,6-tris(4-fluorophenyl)-4-iodomethyl-4,6-disila-1,8-nonadiene as above prepared at 45° C. for 5 hrs. The reactants were separated by silica gel column (eluent: ether) to obtain 4,6,6-tris(4-fluorophenyl)-4,6-disila-4-(1H-1,2,4-triazole-1-ylmethyl)-1,8-nonadiene.

$^1$H-NMR(CCl$_4$, $\delta$): 0.7(s, 2H); 1.5–2.0(m, 4H); 3.7(s, 2H); 4.9–5.2(m, 4H): 5.4–6.1(m, 2H); 6.9–7.9(m, 14H)

EXAMPLE 40

Preparation of
6-(4-ethoxyphenyl)-4,6-bis(4-fluorophenyl)-4,6-disila-4-(1H-1,2,4-triazole-1-ylmethyl)-1,8-nonadiene In the same method as Example 26 were reacted 2.7 g (18 mmol) of NaI and 12.3 g of the mixture of the reaction products containing 4-chloromethyl-6-(4-ethoxyphenyl)-4,6-bis(4-fluorophenyl)-4,6-disila-1,8-nonadiene to carry out the halogen exchange reaction.

In the same method as Example 26 were reacted 0.5 g (15 mmol) of NaH and 1.0 g (15 mmol) of 1,2,4-triazole to obtain the sodium salt of triazole. The salt was reacted with 14.3 g of the mixture containing 6-(4-ethoxyphenyl)-4,6-bis(4-fluorophenyl)-4-iodomethyl-4,6-disila-1,8-nonadiene as above prepared at 50° C. for 5 hrs. The reactants were separated by silica gel column (eluent: ether) to obtain 2.3 g of 6-(4-ethoxyphenyl)-4,6-bis(4-fluorophenyl)-4,6-disila-4-(1H-1,2,4-triazole-1-ylmethyl)-1,8-nonadiene.

$^1$H-NMR(CCl$_4$, $\delta$): 0.7(s, 2H); 1.5–2.0(m, 4H); 3.7(s, 2H); 3.7(s, 2H); 5.0–5.2(m, 4H): 5.4–6.2(m, 2H); 6.8–7.9(m, 14H)

EXAMPLE 41

Preparation of
6,6-bis(4-ethoxyphenyl)-4,4-diphenyl-4,6-disila-7-(1H-1,2,4-triazole-1-ylmethyl)-1-heptene.

In the same method as Example 26 were reacted 1.8 g (12 mmol) of NaI and 8.3 g of the mixture containing 7-chloro-6,6-bis(4-ethoxyphenyl)-4,4-diphenyl-4,6-disila-1-heptene to carry out the halogen exchange reaction.

In the same method as Example 26 were reacted 0.3 g (10 mmol) of NaH and 0.7 g (10 mmol) of 1,2,4-triazole to obtain the sodium salt of triazole. The salt was reacted with 10.2 g of the compounds containing 6,6-bis(4-ethoxyphenyl)-7-iodo-4,4-diphenyl-4,6-disila-1-heptene as above prepared at 45° C. for 5 hrs. The reactants were separated by silica gel column (eluent: ether) to obtain 1.6 g of 6,6-bis(4-ethoxyphenyl)-4,4-diphenyl-4,6-disila-7-(1H-1,2,4-triazole-1-ylmethyl)-1-heptene.

$^1$H-NMR(CCl$_4$, $\delta$): 0.7(s, 2H); 1.8(d, 2H); 4.1(s, 2H); 4.5–4.9(m, 2H): 5.2–5.6(m, 1H); 7.0–7.9(m, 18H)

The compounds listed in Table 1 were converted to the corresponding triazole compounds according to the procedure described in Examples 24 through 41 and the converted compounds are listed in Table 5. In the same manner, the compounds listed in Table 2, Table 3, and Table 4 were converted to the corresponding triazole compounds and they are listed in Table 6, Table 7, and Table 8 respectively.

TABLE 5

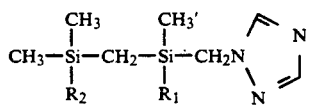

| Substituents | | NMR data (ppm) | | | | | | | |
|---|---|---|---|---|---|---|---|---|---|
| R₁ | R₂ | CH₃ | CH₃' | Si—CH₂ | CH₂—N | triazole-H | R₁ | R₂ | |
| 4-fluorophenyl | CH₃ | 0.3 | 0.4 | 0.5 | 3.7 | 7.8 | 7.0–7.7 | 0.3 | |
| 4-methoxyphenyl | CH₃ | 0.4 | 0.5 | 0.6 | 3.7 | 7.7 | 6.9–7.6 | 0.4 | (24) |
| 4-phenylphenyl | CH₃ | 0.3 | 0.4 | 0.5 | 3.7 | 7.7 | 7.5 | 0.3 | (25) |
| 4-chlorophenyl | 4-fluorophenyl | 0.2 | 0.3 | 0.4 | 3.6 | 7.6 | 7.2 | 6.7–7.4 | (29) |
| 4-ethoxyphenyl | 4-fluorophenyl | 0.2 | 0.5 | 0.6 | 3.7 | 7.7 | 6.7–7.5 | 6.8–7.5 | |
| 4-fluorophenyl | 4-fluorophenyl | 0.2 | 0.3 | 0.4 | 3.7 | 7.7 | 6.8–7.5 | 6.8–7.5 | (26) |
| 4-methoxyphenyl | 4-chlorophenyl | 0.2 | 0.3 | 0.4 | 3.9 | 7.6 | 6.8–7.5 | 7.2 | |
| 4-chlorophenyl | 4-chlorophenyl | 0.2 | 0.3 | 0.4 | 3.9 | 7.6 | 7.2 | 7.2 | |
| 4-fluorophenyl | 4-chlorophenyl | 0.2 | 0.3 | 0.4 | 3.7 | 7.6 | 6.8–7.4 | 7.3 | |
| 4-phenylphenyl | 4-chlorophenyl | 0.2 | 0.4 | 0.6 | 3.7 | 7.7 | 7.6 | 7.2 | |
| 4-methoxyphenyl | 4-methoxyphenyl | 0.3 | 0.4 | 0.5 | 3.8 | 7.8 | 6.9–7.6 | 6.9–7.6 | |
| 4-ethoxyphenyl | 4-methoxyphenyl | 0.4 | 0.5 | 0.6 | 3.7 | 7.7 | 6.8–7.4 | 6.9–7.6 | |
| 4-phenylphenyl | 4-methoxyphenyl | 0.3 | 0.4 | 0.5 | 3.7 | 7.6 | 7.5 | 6.8–7.5 | |
| 4-fluorophenyl | 4-ethoxyphenyl | 0.2 | 0.3 | 0.4 | 3.7 | 7.6 | 6.7–7.3 | 6.7–7.3 | (28) |
| 4-methoxyphenyl | 4-ethoxyphenyl | 0.3 | 0.4 | 0.5 | 3.8 | 7.7 | 7.0–7.7 | 6.8–7.4 | |
| 4-phenylphenyl | 4-ethoxyphenyl | 0.3 | 0.4 | 0.5 | 3.7 | 7.7 | 7.4 | 6.8–7.4 | |
| 4-ethoxyphenyl | 4-phenylphenyl | 0.4 | 0.5 | 0.6 | 3.8 | 7.8 | 6.8–7.4 | 6.9–7.6 | |
| 4-phenylphenyl | 4-phenylphenyl | 0.4 | 0.5 | 0.6 | 3.7 | 7.8 | 7.6 | 7.6 | |
| 4-fluorophenyl | 4-phenylphenyl | 0.3 | 0.4 | 0.5 | 3.7 | 7.7 | 6.9–7.5 | 7.5 | |
| 4-fluorophenyl | 4-fluorobenzyl | −0.1<br>−0.2 | 0.4 | 0.2 | 3.8 | 7.8 | 6.9–7.6 | 7.2 | (27) |
| 4-chlorophenyl | 4-fluorobenzyl | −0.1<br>−0.2 | 0.3 | 0.1 | 3.7 | 7.5 | 7.2 | 6.7 | |
| 4-methoxyphenyl | 4-fluorobenzyl | −0.1<br>0 | 0.4 | 0.3 | 3.8 | 7.7 | 6.8–7.6 | 7.0 | |

TABLE 6

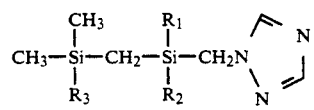

| Substituents | | | NMR data (ppm) | | | | | | | |
|---|---|---|---|---|---|---|---|---|---|---|
| R₁ | R₂ | R₃ | CH₃ | Si—CH₂ | CH₂—N< | triazole-H | R₁ | R₂ | R₃ | |
| 4-methoxyphenyl | 4-methoxyphenyl | CH₃ | 0.1 | 0.5 | 4.3 | 7.8 | 7.0–7.7 | 7.0–7.7 | 0.1 | |
| 4-methoxyphenyl | 4-phenylphenyl | CH₃ | 0 | 0.5 | 4.3 | 7.7 | 6.9–7.6 | 7.6 | 0 | |
| 4-methoxyphenyl | 4-ethoxyphenyl | CH₃ | −0.1 | 0.3 | 4.1 | 7.7 | 6.9–7.6 | 6.8–7.4 | −0.1 | |
| 4-fluorophenyl | 4-chlorophenyl | CH₃ | −0.1 | 0.4 | 4.1 | 7.7 | 7.0–7.5 | 7.3 | −0.1 | |
| 4-fluorophenyl | 4-methoxyphenyl | CH₃ | 0 | 0.4 | 4.3 | 7.8 | 7.1–7.5 | 7.1–7.6 | 0 | |
| 4-fluorophenyl | 4-fluorophenyl | CH₃ | −0.1 | 0.4 | 4.2 | 7.7 | 7.0–7.5 | 7.0–7.5 | −0.1 | |
| 4-phenylphenyl | 4-fluorophenyl | CH₃ | 0.1 | 0.5 | 4.3 | 7.8 | 7.7 | 7.0–7.5 | 0.1 | |
| 4-chlorophenyl | 4-chlorophenyl | CH₃ | 0 | 0.3 | 4.3 | 7.8 | 7.3 | 7.3 | 0 | (30) |
| 4-chlorophenyl | 4-methoxyphenyl | CH₃ | −0.1 | 0.4 | 4.2 | 7.7 | 7.2 | 7.0–7.7 | −0.1 | |
| 4-chlorophenyl | 4-phenylphenyl | CH₃ | −0.1 | 0.5 | 4.3 | 7.8 | 7.2 | 7.0–7.6 | −0.1 | |
| 4-ethoxyphenyl | 4-chlorophenyl | CH₃ | 0 | 0.4 | 4.2 | 7.7 | 6.8–7.4 | 7.3 | 0 | |
| 4-ethoxyphenyl | 4-ethoxyphenyl | CH₃ | −0.1 | 0.4 | 4.2 | 7.6 | 6.9–7.4 | 6.9–7.4 | −0.1 | |
| 4-ethoxyphenyl | 4-phenylphenyl | CH₃ | 0 | 0.5 | 4.3 | 7.7 | 6.8–7.5 | 7.7 | 0 | |
| 4-methoxyphenyl | 4-chlorophenyl | 4-fluorophenyl | 0.2 | 0.4 | 4.2 | 7.8 | 7.0–7.7 | 7.3 | 6.7–7.4 | |
| 4-methoxyphenyl | 4-methoxyphenyl | 4-fluorophenyl | 0.2 | 0.5 | 4.3 | 7.7 | 7.0–7.7 | 7.0–7.7 | 6.8–7.5 | |
| 4-ethoxyphenyl | 4-ethoxyphenyl | 4-fluorophenyl | 0.2 | 0.4 | 4.2 | 7.6 | 6.7–7.4 | 6.7–7.4 | 6.7–7.4 | (31) |
| 4-methoxyphenyl | 4-phenylphenyl | 4-fluorophenyl | 0.3 | 0.5 | 4.3 | 7.8 | 7.0–7.6 | 7.7 | 6.7–7.5 | |
| 4-chlorophenyl | 4-chlorophenyl | 4-fluorophenyl | 0.2 | 0.4 | 4.3 | 7.7 | 7.3 | 7.3 | 6.7–7.5 | |
| 4-chlorophenyl | 4-ethoxyphenyl | 4-fluorophenyl | 0.2 | 0.5 | 4.2 | 7.6 | 7.2 | 6.7–7.3 | 6.7–7.4 | |
| 4-phenylphenyl | 4-fluorophenyl | 4-fluorophenyl | 0.3 | 0.6 | 4.3 | 7.8 | 7.6 | 7.3 | 6.7–7.3 | |
| 4-fluorophenyl | 4-fluorophenyl | 4-fluorophenyl | 0.3 | 0.5 | 4.2 | 7.7 | 6.9–7.6 | 6.9–7.6 | 6.9–7.6 | |
| 4-fluorophenyl | 4-chlorophenyl | 4-fluorophenyl | 0.2 | 0.5 | 4.2 | 7.6 | 6.9–7.6 | 7.3 | 6.8–7.5 | |
| 4-fluorophenyl | 4-ethoxyphenyl | 4-fluorophenyl | 0.2 | 0.4 | 4.1 | 7.7 | 6.8–7.7 | 6.9–7.5 | 6.8–7.5 | |
| 4-ethoxyphenyl | 4-phenylphenyl | 4-fluorophenyl | 0.3 | 0.6 | 4.2 | 7.7 | 6.9–7.4 | 7.7 | 6.7–7.4 | |
| 4-methoxyphenyl | 4-methoxyphenyl | 4-chlorophenyl | 0.2 | 0.5 | 4.0 | 7.6 | 7.1–7.6 | 7.1–7.6 | 7.3 | |
| 4-methoxyphenyl | 4-ethoxyphenyl | 4-chlorophenyl | 0.2 | 0.5 | 4.2 | 7.7 | 7.0–7.6 | 6.9–7.6 | 7.2 | (32) |
| 4-fluorophenyl | 4-chlorophenyl | 4-chlorophenyl | 0.2 | 0.6 | 4.1 | 7.8 | 7.0–7.5 | 7.3 | 7.3 | |
| 4-fluorophenyl | 4-fluorophenyl | 4-chlorophenyl | 0.2 | 0.5 | 4.1 | 7.8 | 7.0–7.5 | 7.0–7.5 | 7.2 | (33) |
| 4-fluorophenyl | 4-ethoxyphenyl | 4-chlorophenyl | 0.2 | 0.4 | 4.1 | 7.7 | 7.0–7.6 | 7.0–7.5 | 7.2 | |
| 4-chlorophenyl | 4-methoxyphenyl | 4-chlorophenyl | 0.2 | 0.5 | 4.2 | 7.8 | 7.3 | 7.0–7.7 | 7.3 | |
| 4-chlorophenyl | 4-chlorophenyl | 4-chlorophenyl | 0.3 | 0.6 | 4.2 | 7.8 | 7.4 | 7.4 | 7.4 | |
| 4-phenylphenyl | 4-fluorophenyl | 4-chlorophenyl | 0.3 | 0.6 | 4.3 | 7.8 | 7.7 | 7.1–7.6 | 7.3 | |
| 4-ethoxyphenyl | 4-ethoxyphenyl | 4-chlorophenyl | 0.2 | 0.5 | 4.2 | 7.7 | 7.0–7.6 | 7.0–7.6 | 7.2 | |

TABLE 6-continued

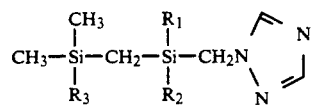

| Substituents | | | NMR data (ppm) | | | | | | |
|---|---|---|---|---|---|---|---|---|---|
| $R_1$ | $R_2$ | $R_3$ | $CH_3$ | $Si-CH_2$ | $CH_2-N$ | triazole-H | $R_1$ | $R_2$ | $R_3$ |
| 4-ethoxyphenyl | 4-chlorophenyl | 4-chlorophenyl | 0.2 | 0.4 | 4.1 | 7.7 | 7.0–7.5 | 7.3 | 7.3 |
| 4-methoxyphenyl | 4-phenylphenyl | 4-methoxyphenyl | 0.3 | 0.6 | 4.3 | 7.8 | 7.1–7.6 | 7.7 | 7.1–7.6 |
| 4-methoxyphenyl | 4-methoxyphenyl | 4-methoxyphenyl | 0.2 | 0.4 | 4.1 | 7.7 | 7.0–7.6 | 7.0–7.6 | 7.0–7.6 |
| 4-methoxyphenyl | 4-ethoxyphenyl | 4-methoxyphenyl | 0.2 | 0.4 | 4.2 | 7.7 | 7.1–7.6 | 7.0–7.5 | 7.1–7.6 |
| 4-chlorophenyl | 4-chlorophenyl | 4-methoxyphenyl | 0.2 | 0.5 | 4.2 | 7.7 | 7.4 | 7.4 | 7.0–7.5 |
| 4-chlorophenyl | 4-methoxyphenyl | 4-methoxyphenyl | 0.2 | 0.4 | 4.1 | 7.7 | 7.3 | 7.0–7.6 | 7.0–7.6 |
| 4-ethoxyphenyl | 4-fluorophenyl | 4-methoxyphenyl | 0.2 | 0.5 | 4.1 | 7.7 | 7.1–7.5 | 7.2–7.6 | 7.0–7.5 |
| 4-ethoxyphenyl | 4-ethoxyphenyl | 4-methoxyphenyl | 0.2 | 0.4 | 4.2 | 7.6 | 7.1–7.6 | 7.1–7.6 | 7.0–7.6 |
| 4-fluorophenyl | 4-fluorophenyl | 4-methoxyphenyl | 0.3 | 0.6 | 4.2 | 7.7 | 7.0–7.7 | 7.0–7.7 | 7.0–7.6 |
| 4-fluorophenyl | 4-methoxyphenyl | 4-methoxyphenyl | 0.2 | 0.5 | 4.1 | 7.7 | 7.2–7.6 | 7.2–7.6 | 7.2–7.6 |
| 4-fluorophenyl | 4-chlorophenyl | 4-methoxyphenyl | 0.2 | 0.4 | 4.1 | 7.8 | 7.0–7.5 | 7.3 | 6.9–7.6 |
| 4-phenylphenyl | 4-ethoxyphenyl | 4-methoxyphenyl | 0.3 | 0.6 | 4.2 | 7.8 | 7.6 | 7.0–7.6 | 7.0–7.5 |
| 4-phenylphenyl | 4-chlorophenyl | 4-methoxyphenyl | 0.3 | 0.6 | 4.3 | 7.8 | 7.7 | 7.4 | 7.0–7.6 |
| 4-ethoxyphenyl | 4-ethoxyphenyl | 4-ethoxyphenyl | 0.2 | 0.5 | 4.1 | 7.7 | 7.1–7.6 | 7.1–7.6 | 7.1–7.6 |
| 4-methoxyphenyl | 4-methoxyphenyl | 4-ethoxyphenyl | 0.2 | 0.4 | 4.1 | 7.6 | 7.1–7.6 | 7.1–7.6 | 7.0–7.5 |
| 4-methoxyphenyl | 4-ethoxyphenyl | 4-ethoxyphenyl | 0.2 | 0.4 | 4.2 | 7.7 | 7.2–7.6 | 6.9–7.5 | 6.9–7.5 |
| 4-chlorophenyl | 4-fluorophenyl | 4-ethoxyphenyl | 0.3 | 0.5 | 4.1 | 7.7 | 7.3 | 7.0–7.6 | 6.9–7.5 |
| 4-fluorophenyl | 4-fluorophenyl | 4-phenylphenyl | 0.3 | 0.6 | 4.2 | 7.7 | 7.2–7.7 | 7.0–7.6 | 7.8 |

TABLE 7

$$R_3\text{—Si—CH}_2\text{—Si—CH}_2\text{N} \diagup\!\!\!\diagdown$$ (structure with CH₃, R₁, R₂, R₄ substituents and triazole)

$R_2 = CH_2CH=CH_2$

| Substituents | | | CH₃ | Si—CH₃ | CH₂—N | triazole-H | —CH₂C=C | C—CH=C | C—C=CH₂ | R₁ | R₃ | R₄ | |
|---|---|---|---|---|---|---|---|---|---|---|---|---|---|
| R₁ | R₃ | R₄ | | | | | NMR data (ppm) | | | | | | |
| 2-propenyl | 2-propenyl | 2-propenyl | 0.3 | 0 | 3.8 | 7.8 | 1.6–1.8 | 5.5–6.2 | 4.8–5.0 | | | | |
| 2-propenyl | 4-fluorophenyl | 2-propenyl | −0.1 | 0 | 3.4 | 7.8 | 1.3–2.8 | 5.3–6.0 | 4.7–4.9 | | 6.8–7.5 | | |
| 2-propenyl | 4-phenylphenyl | 2-propenyl | 0.2 | 0.3 | 3.5 | 7.7 | 1.5–3.0 | 5.4–6.0 | 4.8–5.1 | | 7.5 | | |
| 2-propenyl | phenyl | phenyl | 0.2 | 0.4 | 3.5 | 7.7 | 1.4–1.8 | 5.4–6.1 | 4.7–5.0 | | 7.4 | 7.4 | |
| 2-propenyl | 4-ethoxyphenyl | phenyl | 0.1 | 0.3 | 3.4 | 7.8 | 1.3–1.7 | 5.4–6.0 | 4.7–4.9 | | 6.9–7.6 | 7.3 | |
| 2-propenyl | 2-propenyl | phenyl | 0 | 0.2 | 3.5 | 7.7 | 1.2–2.7 | 5.2–5.9 | 4.8–5.0 | | | 7.3 | |
| 2-propenyl | 4-fluorophenyl | phenyl | 0.2 | 0.7 | 3.6 | 7.9 | 1.5–2.3 | 5.4–6.2 | 4.8–5.1 | | 7.1–7.8 | 7.1–7.8 | (35) |
| 2-propenyl | 4-ethoxyphenyl | phenyl | 0.1 | 0.3 | 3.5 | 7.7 | 1.4–1.8 | 5.3–6.0 | 4.7–5.0 | | 6.9–7.7 | 6.8–7.5 | |
| 2-propenyl | 4-phenylphenyl | phenyl | 0.2 | 0.4 | 3.7 | 7.8 | 1.3–1.7 | 5.4–6.1 | 4.7–4.9 | | 7.3 | 7.0–7.6 | (36) |
| 2-propenyl | phenyl | phenyl | 0.2 | 0.4 | 3.6 | 7.6 | 1.2–1.8 | 5.3–6.1 | 4.6–4.9 | | 7.3 | 6.8–7.5 | |
| 2-propenyl | 2-propenyl | 4-ethoxyphenyl | −0.1 | 0 | 3.5 | 7.7 | 1.4–2.8 | 5.3–6.1 | 4.7–4.9 | | 6.8–7.6 | 6.8–7.6 | |
| 2-propenyl | 4-ethoxyphenyl | 4-ethoxyphenyl | 0 | 0.2 | 3.4 | 7.8 | 1.3–1.7 | 5.4–6.1 | 4.7–5.0 | | 7.4 | 6.8–7.6 | |
| 2-propenyl | 4-phenylphenyl | 4-ethoxyphenyl | 0.2 | 0.4 | 3.6 | 7.7 | 1.4–1.8 | 5.3–6.0 | 4.7–4.9 | | 7.4 | 6.7–7.5 | |
| 2-propenyl | 4-phenylphenyl | 4-phenylphenyl | 0.3 | 0.5 | 3.7 | 7.8 | 1.4–1.8 | 5.4–6.1 | 4.7–5.0 | | 7.5 | 7.5 | |
| 2-propenyl | phenyl | 4-phenylphenyl | 0.2 | 0.4 | 3.6 | 7.5 | 1.3–1.7 | 5.3–6.0 | 4.7–4.9 | | 7.3 | 7.4 | |
| 4-ethoxyphenyl | phenyl | phenyl | 0.2 | 0.7 | 3.2 | 7.7 | 1.8 | 5.3–5.7 | 4.7–5.1 | 6.9–7.7 | 7.4 | 7.4 | |
| 4-ethoxyphenyl | phenyl | phenyl | 0.3 | 0.9 | 3.7 | 7.8 | 2.0 | 5.4–5.8 | 4.7–5.1 | 6.9–7.6 | 7.5 | 7.4 | |
| 4-ethoxyphenyl | 4-phenylphenyl | phenyl | 0.2 | 0.8 | 3.7 | 7.7 | 1.9 | 5.3–5.7 | 4.6–5.0 | 6.8–7.7 | 7.5 | 7.4 | |
| 4-ethoxyphenyl | 4-fluorophenyl | 4-fluorophenyl | 0.1 | 0.7 | 3.4 | 7.7 | 1.8 | 5.2–5.6 | 4.6–5.0 | 6.9–7.7 | 6.9–7.7 | 6.9–7.7 | |
| 4-ethoxyphenyl | 4-ethoxyphenyl | 4-fluorophenyl | 0.3 | 0.8 | 3.3 | 7.7 | 2.1 | 5.4–5.8 | 4.7–5.2 | 6.9–7.7 | 6.8–7.6 | 6.8–7.6 | |
| 4-ethoxyphenyl | 4-phenylphenyl | 4-fluorophenyl | 0.2 | 0.7 | 3.7 | 7.8 | 1.8 | 5.3–5.7 | 4.5–4.9 | 6.8–7.7 | 7.5 | 6.9–7.7 | |
| 4-ethoxyphenyl | phenyl | 4-fluorophenyl | 0.1 | 0.6 | 3.5 | 7.7 | 2.1 | 5.2–5.7 | 4.5–4.9 | 6.8–7.6 | 7.3 | 6.9–7.6 | |
| 4-ethoxyphenyl | 4-ethoxyphenyl | 4-ethoxyphenyl | 0.3 | 0.9 | 3.7 | 7.8 | 2.0 | 5.3–5.7 | 4.7–5.1 | 6.8–7.6 | 6.8–7.6 | 6.8–7.6 | |
| 4-ethoxyphenyl | 4-phenylphenyl | 4-ethoxyphenyl | 0.3 | 0.7 | 3.6 | 7.7 | 1.7 | 5.0–5.4 | 4.4–4.8 | 6.7–7.5 | 7.4 | 6.8–7.6 | |
| 4-ethoxyphenyl | phenyl | 4-ethoxyphenyl | 0.2 | 0.7 | 3.6 | 7.8 | 2.1 | 5.4–5.8 | 4.7–5.1 | 6.7–7.5 | 7.5 | 6.7–7.5 | |
| 4-ethoxyphenyl | 4-phenylphenyl | 4-phenylphenyl | 0.3 | 0.9 | 3.8 | 7.8 | 1.9 | 5.3–5.7 | 4.6–5.0 | 6.8–7.6 | 6.8–7.6 | 6.8–7.6 | |
| 4-ethoxyphenyl | 4-fluorophenyl | 4-phenylphenyl | 0.2 | 0.8 | 3.0 | 7.7 | 1.8 | 5.2–5.6 | 4.5–4.9 | 6.7–7.6 | 6.8–7.6 | 6.7–7.6 | |
| 4-fluorophenyl | 4-fluorophenyl | 4-ethoxyphenyl | 0.2 | 0.7 | 3.4 | 7.8 | 1.9 | 5.3–5.8 | 4.5–4.9 | 6.8–7.5 | 7.2 | 6.8–7.5 | (34) |
| 4-fluorophenyl | 4-ethoxyphenyl | 4-fluorophenyl | 0.2 | 0.7 | 3.4 | 7.7 | 1.8 | 5.3–5.8 | 4.7–5.1 | 6.9–7.6 | 7.6 | 6.9–7.6 | |
| 4-fluorophenyl | 4-phenylphenyl | 4-fluorophenyl | 0.3 | 0.8 | 3.6 | 7.8 | 2.1 | 5.5–5.9 | 4.7–5.1 | 6.9–7.7 | 7.6 | 6.9–7.6 | |
| 4-fluorophenyl | 4-ethoxyphenyl | 4-ethoxyphenyl | 0.2 | 0.7 | 3.5 | 7.7 | 1.7 | 5.1–5.5 | 4.4–4.7 | 6.8–7.6 | 6.8–7.6 | 68–7.6 | |
| 4-fluorophenyl | phenyl | 4-ethoxyphenyl | 0.2 | 0.8 | 3.6 | 7.7 | 1.8 | 5.2–5.6 | 4.6–5.0 | 6.8–7.6 | 7.1 | 6.9–7.6 | |
| 4-fluorophenyl | phenyl | phenyl | 0.2 | 0.7 | 3.5 | 7.7 | 1.8 | 5.3–5.6 | 4.6–5.1 | 6.9–7.7 | 7.2 | 7.2 | |
| 4-fluorophenyl | 4-phenylphenyl | phenyl | 0.3 | 0.8 | 3.6 | 7.8 | 2.0 | 5.4–5.8 | 4.7–5.1 | 6.8–7.6 | 7.4 | 7.3 | |
| 4-fluorophenyl | 4-phenylphenyl | 4-phenylphenyl | 0.4 | 0.9 | 3.7 | 7.8 | 2.2 | 5.5–5.8 | 4.8–5.1 | 6.9–7.7 | 7.5 | 7.5 | |
| 4-fluorophenyl | 4-ethoxyphenyl | 4-phenylphenyl | 0.3 | 0.8 | 3.5 | 7.7 | 1.9 | 5.3–5.7 | 4.6–5.0 | 7.1–7.8 | 6.9–7.7 | 7.4 | |

TABLE 8

$$R_4-\underset{\underset{R_5}{|}}{\overset{\overset{R_3}{|}}{Si}}-CH_2-\underset{\underset{R_2}{|}}{\overset{\overset{R_1}{|}}{Si}}-CH_2N{\diagdown\!\!\!\diagup}\!\!\!\!{\underset{N}{\overset{N}{|}}}$$

$R_3=CH_2CH=CH_2$

| Substituents | | | | NMR data (ppm) | | | | | | | | | | |
|---|---|---|---|---|---|---|---|---|---|---|---|---|---|---|
| R₁ | R₂ | R₄ | R₅ | Si—CH₂ | CH₂—N | triazole-H | CH₂—C≡C | C—CH= | C—C=CH₂ | R₁ | R₂ | R₄ | R₅ | |
| 2-propenyl | 2-propenyl | 4-ethoxyphenyl | 4-ethoxyphenyl | 0.3 | 3.6 | 7.8 | 1.4–2.9 | 5.4–6.1 | 4.8–5.0 | | | 6.8–7.6 | 6.8–7.6 | |
| 2-propenyl | 2-propenyl | 4-phenylphenyl | 4-ethoxyphenyl | 0.6 | 3.7 | 7.8 | 1.5–3.0 | 5.5–6.1 | 4.9–5.1 | | | 7.5 | 6.9–7.7 | (38) |
| 2-propenyl | 2-propenyl | phenyl | 4-ethoxyphenyl | 0.5 | 3.6 | 7.7 | 1.3–2.8 | 5.2–6.0 | 4.7–4.9 | | | 7.3 | 6.8–7.6 | |
| 2-propenyl | 2-propenyl | phenyl | phenyl | 0.4 | 3.6 | 7.8 | 1.4–2.8 | 5.3–6.0 | 4.6–4.8 | | | 7.3 | 7.3 | |
| 2-propenyl | 2-propenyl | 4-fluorophenyl | phenyl | 0.5 | 3.5 | 7.7 | 1.4–2.9 | 5.3–6.0 | 4.6–4.9 | | | 7.0–7.7 | 7.4 | |
| 2-propenyl | 2-propenyl | 4-phenylphenyl | phenyl | 0.5 | 3.7 | 7.8 | 1.5–2.9 | 5.4–6.0 | 4.9–5.1 | | | 7.4 | 7.3 | (37) |
| 2-propenyl | 2-propenyl | 4-fluorophenyl | 4-fluorophenyl | 0.8 | 3.6 | 7.9 | 1.6–3.1 | 5.5–6.2 | 4.9–5.2 | | | 7.1–7.8 | 7.1–7.8 | |
| 2-propenyl | 2-propenyl | 4-ethoxyphenyl | 4-fluorophenyl | 0.6 | 3.5 | 7.8 | 1.5–2.9 | 5.4–6.1 | 4.8–5.0 | | | 7.0–7.7 | 7.1–7.8 | |
| 2-propenyl | 2-propenyl | phenyl | 2-propenyl | 0.2 | 3.5 | 7.8 | 1.4–2.9 | 5.4–6.1 | 4.9–5.1 | | | 7.2 | | |
| 2-propenyl | 2-propenyl | 4-fluorophenyl | 2-propenyl | 0.2 | 3.4 | 7.9 | 1.5–2.9 | 5.4–6.0 | 4.8–5.0 | | | 7.0–7.5 | | |
| 2-propenyl | 2-propenyl | 4-ethoxyphenyl | 2-propenyl | 0.1 | 3.4 | 7.8 | 1.3–2.8 | 5.3–6.0 | 4.7–4.9 | | | 6.7–7.5 | | |
| 2-propenyl | 2-propenyl | 4-phenylphenyl | 2-propenyl | 0.3 | 3.6 | 7.8 | 1.5–3.0 | 5.4–6.1 | 4.8–5.0 | | | 7.4 | | |
| 2-propenyl | 2-propenyl | 4-fluorophenyl | 4-phenylphenyl | 0.6 | 3.7 | 7.9 | 1.6–3.1 | 5.6–6.3 | 5.0–5.2 | | | 7.1–7.8 | 7.5 | |
| 4-fluorophenyl | 4-fluorophenyl | phenyl | phenyl | 0.8 | 4.0 | 7.7 | 1.8 | 5.2–5.8 | 4.5–4.9 | 7.0–7.6 | 7.0–7.7 | 7.3 | 7.3 | |
| 4-fluorophenyl | 4-fluorophenyl | 4-ethoxyphenyl | phenyl | 0.9 | 3.9 | 7.8 | 1.8 | 5.3–5.8 | 4.6–4.9 | 7.0–7.7 | 7.0–7.7 | 6.8–7.6 | 7.2 | |
| 4-fluorophenyl | 4-fluorophenyl | 4-phenylphenyl | phenyl | 1.0 | 4.0 | 7.8 | 1.9 | 5.3–5.7 | 4.6–5.0 | 7.0–7.6 | 7.0–7.6 | 7.4 | 7.3 | |
| 4-fluorophenyl | 4-fluorophenyl | 4-fluorophenyl | phenyl | 0.7 | 4.1 | 7.7 | 1.8 | 5.3–5.7 | 4.5–4.9 | 6.9–7.7 | 6.9–7.7 | 6.9–7.7 | 7.2 | |
| 4-fluorophenyl | 4-fluorophenyl | 4-ethoxyphenyl | 4-ethoxyphenyl | 0.5 | 4.2 | 7.8 | 1.6 | 5.4–5.8 | 4.7–5.0 | 6.9–7.7 | 6.9–7.6 | 6.8–7.6 | 6.8–7.6 | |
| 4-fluorophenyl | 4-fluorophenyl | 4-phenylphenyl | 4-ethoxyphenyl | 0.7 | 4.1 | 7.7 | 1.7 | 5.3–6.0 | 4.8–5.1 | 6.9–7.6 | 6.9–7.7 | 7.4 | 6.9–7.7 | |
| 4-fluorophenyl | 4-fluorophenyl | phenyl | 4-ethoxyphenyl | 0.6 | 4.1 | 7.9 | 1.8 | 5.3–5.7 | 4.7–5.1 | 6.9–7.7 | 6.9–7.7 | 6.9–7.7 | 6.8–7.6 | |
| 4-fluorophenyl | 4-fluorophenyl | 4-fluorophenyl | 4-ethoxyphenyl | 0.9 | 4.2 | 7.8 | 2.0 | 5.4–5.8 | 4.8–5.2 | 7.0–7.8 | 7.0–7.8 | 7.0–7.8 | 7.0–7.8 | |
| 4-fluorophenyl | 4-fluorophenyl | 4-phenylphenyl | 4-fluorophenyl | 1.0 | 4.2 | 7.9 | 2.1 | 5.4–5.9 | 4.9–5.2 | 7.1–7.8 | 7.1–7.8 | 7.6 | 7.1–7.8 | |
| 2-propenyl | 4-ethoxyphenyl | phenyl | phenyl | 0.4 | 3.5 | 7.8 | 1.2–1.8 | 5.4–6.1 | 4.8–5.0 | | 6.9–7.7 | 7.4 | 7.4 | |
| 2-propenyl | 4-ethoxyphenyl | 4-phenylphenyl | phenyl | 0.6 | 3.6 | 7.8 | 1.5–2.3 | 5.5–6.2 | 4.8–5.1 | | 6.9–7.7 | 7.4 | 7.3 | |
| 2-propenyl | 4-ethoxyphenyl | 4-ethoxyphenyl | 4-fluorophenyl | 0.8 | 3.6 | 7.9 | 1.4–2.0 | 5.4–6.2 | 4.6–4.9 | | 6.8–7.6 | 7.1–7.7 | 7.1–7.7 | |
| 2-propenyl | 4-ethoxyphenyl | 4-phenylphenyl | 4-fluorophenyl | 0.9 | 3.6 | 7.9 | 1.6–2.4 | 5.6–6.3 | 4.8–5.1 | | 6.9–7.7 | 7.5 | 7.5 | |
| 2-propenyl | 4-ethoxyphenyl | phenyl | 4-fluorophenyl | 0.6 | 3.7 | 7.8 | 1.3–1.8 | 5.4–6.1 | 4.7–5.0 | | 6.8–7.6 | 7.3 | 7.3 | |
| 2-propenyl | 4-ethoxyphenyl | 4-fluorophenyl | 4-fluorophenyl | 0.7 | 3.5 | 7.7 | 1.4–1.9 | 5.4–6.1 | 4.8–5.1 | | 6.9–7.7 | 6.9–7.7 | 7.0–7.7 | |
| 2-propenyl | 4-ethoxyphenyl | 4-phenylphenyl | 4-ethoxyphenyl | 0.9 | 3.6 | 7.9 | 1.6–2.4 | 5.4–6.1 | 4.8–5.2 | | 7.0–7.8 | 7.5 | 7.0–7.8 | |
| 2-propenyl | 4-ethoxyphenyl | 4-fluorophenyl | 4-ethoxyphenyl | 0.8 | 3.6 | 7.8 | 1.5–2.1 | 5.3–6.0 | 4.9–5.2 | | 6.9–7.7 | 6.8–7.6 | 7.0–7.7 | |
| 2-propenyl | 4-ethoxyphenyl | 4-fluorophenyl | 4-ethoxyphenyl | 0.5 | 3.5 | 7.7 | 1.3–1.8 | 5.2–5.9 | 4.7–5.0 | | 6.8–7.6 | 7.2 | 6.8–7.6 | |
| 4-ethoxyphenyl | 4-ethoxyphenyl | phenyl | phenyl | 0.7 | 4.1 | 7.8 | 1.8 | 5.3–5.6 | 4.5–4.9 | 7.0–7.7 | 6.9–7.7 | 7.3 | 7.3 | |
| 4-ethoxyphenyl | 4-ethoxyphenyl | 4-fluorophenyl | phenyl | 0.9 | 4.0 | 7.8 | 2.0 | 5.3–5.7 | 4.6–4.9 | 7.1–7.7 | 7.1–7.7 | 6.9–7.6 | 7.4 | (41) |
| 4-ethoxyphenyl | 4-ethoxyphenyl | 4-ethoxyphenyl | 4-phenylphenyl | 0.7 | 4.1 | 7.8 | 1.9 | 5.2–5.5 | 4.5–4.7 | 7.0–7.7 | 7.0–7.7 | 7.0–7.7 | 7.3 | |
| 4-ethoxyphenyl | 4-ethoxyphenyl | phenyl | 4-fluorophenyl | 1.1 | 4.2 | 7.8 | 2.1 | 5.5–5.9 | 5.1–5.3 | 7.1–7.8 | 7.1–7.7 | 7.5 | 7.0–7.7 | |
| 4-ethoxyphenyl | 4-ethoxyphenyl | 4-ethoxyphenyl | 4-fluorophenyl | 0.8 | 4.0 | 7.7 | 1.9 | 5.3–5.7 | 4.6–4.9 | 7.1–7.7 | 7.1–7.7 | 7.1–7.7 | 7.0–7.7 | |
| 4-ethoxyphenyl | 4-ethoxyphenyl | 4-fluorophenyl | 4-ethoxyphenyl | 0.7 | 4.1 | 7.8 | 1.8 | 5.3–5.6 | 4.6–4.8 | 6.9–7.6 | 6.9–7.6 | 6.9–7.6 | 7.0–7.7 | |
| 2-propenyl | phenyl | phenyl | 4-ethoxyphenyl | 0.7 | 3.7 | 7.8 | 1.5–2.0 | 5.4–6.1 | 4.9–5.2 | | 6.9–7.7 | 7.3 | 6.9–7.7 | (39) |
| 2-propenyl | 4-fluorophenyl | 4-fluorophenyl | 4-fluorophenyl | 0.6 | 3.6 | 7.7 | 1.3–1.8 | 5.3–6.0 | 4.8–5.0 | | 6.8–7.6 | 7.2 | 7.2 | |
| 2-propenyl | 4-fluorophenyl | 4-phenylphenyl | phenyl | 0.9 | 3.8 | 7.8 | 1.6–2.2 | 5.5–6.2 | 5.0–5.2 | | 6.8–7.7 | 7.4 | 7.3 | |

TABLE 8-continued $$R_4-Si-CH_2-Si-CH_2N\begin{matrix}N\\\|\\N\end{matrix}$$ with $R_3$, $R_5$ on Si $R_3$=CH$_2$CH=CH$_2$

| Substituents | | | | | NMR data (ppm) | | | | | | | | | | |
|---|---|---|---|---|---|---|---|---|---|---|---|---|---|---|---|
| R$_1$ | R$_2$ | R$_4$ | R$_5$ | Si—CH$_2$ | CH$_2$—N | triazole-H | CH$_2$—C=C | C—CH=C | C—C=CH$_2$ | R$_1$ | R$_2$ | R$_4$ | R$_5$ | |
| 2-propenyl | 4-fluorophenyl | 4-ethoxyphenyl | 4-ethoxyphenyl | 0.7 | 3.7 | 7.7 | 1.4-2.0 | 5.3-6.1 | 4.9-5.1 | | 6.8-7.6 | 6.8-7.6 | 6.8-7.6 | (40) |
| 2-propenyl | 4-fluorophenyl | 4-fluorophenyl | 4-ethoxyphenyl | 0.7 | 3.7 | 7.8 | 1.5-2.0 | 5.4-6.2 | 5.0-5.2 | | 6.8-7.7 | 6.8-7.7 | 6.8-7.6 | |
| 2-propenyl | 4-fluorophenyl | phenyl | 4-ethoxyphenyl | 0.6 | 3.7 | 7.7 | 1.3-1.7 | 5.4-6.0 | 4.9-5.0 | | 6.8-7.6 | 7.2 | 6.7-7.6 | |
| 2-propenyl | 4-fluorophenyl | 4-phenylphenyl | 4-ethoxyphenyl | 0.8 | 3.8 | 7.8 | 1.7-2.3 | 5.5-6.2 | 4.9-5.1 | | 6.8-7.6 | 7.5 | 6.9-7.7 | |
| 2-propenyl | 4-fluorophenyl | 4-fluorophenyl | 4-phenylphenyl | 0.9 | 3.8 | 7.8 | 1.8-2.4 | 5.5-6.3 | 4.8-5.1 | | 6.9-7.7 | 6.9-7.7 | 7.5 | |
| 4-fluorophenyl | 4-ethoxyphenyl | 4-ethoxyphenyl | 4-ethoxyphenyl | 0.8 | 4.0 | 7.8 | 1.7 | 5.2-5.6 | 4.6-4.9 | 6.8-7.6 | 6.8-7.6 | 6.8-7.6 | 6.8-7.6 | |
| 4-fluorophenyl | 4-ethoxyphenyl | 4-phenylphenyl | 4-ethoxyphenyl | 0.9 | 4.1 | 7.8 | 1.9 | 5.3-5.7 | 4.8-5.1 | 6.9-7.7 | 6.9-7.6 | 7.5 | 6.9-7.6 | |
| phenyl | phenyl | phenyl | phenyl | 0.7 | 4.0 | 7.7 | 1.6 | 5.1-5.5 | 4.5-4.8 | 68-7.6 | 6.8-7.6 | 7.2 | 7.2 | |
| 4-fluorophenyl | 4-ethoxyphenyl | 4-phenylphenyl | phenyl | 0.8 | 4.1 | 7.8 | 1.9 | 5.2-5.6 | 4.7-5.0 | 6.9-7.7 | 6.9-7.7 | 7.4 | 7.3 | |
| 4-fluorophenyl | 4-ethoxyphenyl | 4-fluorophenyl | 4-fluorophenyl | 0.8 | 4.1 | 7.7 | 1.9 | 5.3-5.7 | 4.7-5.1 | 6.9-7.7 | 6.9-7.7 | 6.9-7.7 | 6.9-7.7 | |
| 4-fluorophenyl | 4-ethoxyphenyl | 4-ethoxyphenyl | 4-ethoxyphenyl | 0.7 | 4.0 | 7.7 | 1.8 | 5.2-5.7 | 4.6-5.0 | 6.9-7.6 | 6.8-7.6 | 6.8-7.6 | 6.9-7.6 | |
| 4-fluorophenyl | 4-ethoxyphenyl | 4-fluorophenyl | 4-phenylphenyl | 0.9 | 4.2 | 7.8 | 2.0 | 5.3-5.7 | 4.9-5.2 | 7.0-7.7 | 6.8-7.6 | 7.0-7.7 | 7.5 | |

EXAMPLE 42

Bioactivity tests

The compounds of this invention were dissolved respectively in acetone in an amount equal to 10% of the final volume and then in purified water at the concentration of 100 ppm and 50 ppm.

Each of the solution was mixed with potato-sucrose-agar medium in a 6" petri dish and one of the fungi was spotted at the center of the dish. The dish was incubated in growth room for several days. The percent disease control was derived from the radii of spore growth. The screening tests in vitro condition are well-known to those skilled in the art.

The following fungi were used for the screening.
1) Al.; *Alternaria mali*
2) Phy. ca.; *Phytophthora capsisi*
3) Phy. ba.; *Physalospora baccae*
4) Bo.do(Ma); *Botryosphaeria dothidea* Macrophoma sp.
5) Glo.; *Glomerella cingulata*
6) Py.or.; *Pyricalaria oryzae*
7) Rhi.so.; *Rhizoctonia solani*
8) Fu.mo.; *Fusarium moniliforme*
9) Rhi.sp.; *Rhizopus sp.*
10) Bo.ci.; *Botry tris cinerea*

The results of the percent control for the fungi by each compound of this invention are listed in Table 9.

TABLE 9

The percent control of (1H-1,2,4-triazolyl)disilaalkane derivatives to fungi

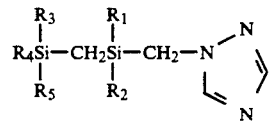

| Compounds | conc. (ppm) | Al. | Phy ca. | Phy ba. | Bo.do (Ma.) | Glo. | Py. or. | Rhy. so. | Fu. mo. | Rhi. sp. | Bo ci. |
|---|---|---|---|---|---|---|---|---|---|---|---|
| 2-(4-fluorophenyl)-2,4,4-trimethyl-2,4-di | 100 | 81 | 31 | 72 | 74 | — | 100 | 90 | 66 | 56 | 83 |
| sila-1-(1H-1,2,4-triazol-1-yl)pentane | 50 | 78 | 20 | 56 | 69 | — | 100 | 90 | 62 | 49 | 81 |
| 2,4-bis(4-fluorophenyl)-2,4-dimethyl,2,4- | 100 | 44 | 6 | 22 | 43 | 73 | 54 | 60 | 38 | 26 | 10 |
| disila-1-(1H-1,2,4-triazol-1-yl)pentane | 50 | 38 | 3 | 22 | 40 | 72 | 50 | 57 | 35 | 24 | 0 |
| 2-(4-chlorophenyl)-4-(4-fluorophenyl)-2,4-di- | 100 | 38 | 0 | 20 | 43 | 73 | 48 | 50 | 58 | 20 | 18 |
| methyl-2,4-disila-1-(1H-1,2,4-triazol-1-yl)pentane | 50 | 38 | 0 | 20 | 43 | 67 | 46 | 31 | 34 | 18 | 13 |
| 4-(4-fluorobenzyl)-2-(4-fluorophenyl)-2,4-di | 100 | 43 | 3 | 30 | 49 | 0 | 57 | 36 | 41 | 24 | 0 |
| methyl-2,4-disila-1-(1H-1,2,4-triazol-1-yl)pentane | 50 | 38 | 3 | 26 | 40 | 0 | 50 | 36 | 34 | 21 | 0 |
| 2-(4-chlorophenyl)-2-(4-fluorophenyl)-2,4-di | 100 | 79 | — | 69 | 79 | 87 | 100 | 96 | 46 | 50 | 90 |
| methyl-1-(1H-1,2,4-triazol-1-yl)pentane | 50 | 75 | — | 69 | 79 | 87 | 100 | 96 | 46 | 50 | 90 |
| 4-(4-ethoxyphenyl)-2-(4-fluorophenyl)-2,4-di | 100 | 72 | 60 | 74 | 78 | 77 | 100 | 78 | 63 | 43 | 66 |
| methyl-2,4-disila-1-(1H-1,2,4-triazol-1-yl)pentane | 50 | 63 | 50 | 53 | 74 | 71 | 100 | 78 | 58 | 19 | 69 |
| 4-(4-chlorophenyl)-2-(4-methoxyphenyl)-2,4-di | 100 | 62 | 59 | 60 | 66 | 82 | 100 | 100 | 41 | 48 | 80 |
| methyl-2,4-disila-1-(1H-1,2,4-triazol-1-yl)-pentane | 50 | 30 | 43 | 50 | 34 | 56 | 100 | 100 | 28 | 32 | 40 |
| 4-(4-chlorophenyl)-2-(4-fluorophenyl)-2,4-di- | 100 | 84 | 54 | 82 | 86 | 0 | 100 | 100 | 69 | 65 | 100 |
| methyl-2,4-disila-1-(1H-1,2,4-triazol-1-yl)pentane | 50 | 84 | 43 | 78 | 74 | 0 | 100 | 93 | 67 | 59 | 100 |
| 2,4-bis(4-chlorophenyl)-2,4-dimethyl-2,4- | 100 | 69 | 22 | 37 | 82 | 76 | 27 | 42 | 57 | 40 | 41 |
| disila-1-(1H-1,2,4-triazol-1-yl)pentane | 50 | 54 | 16 | 34 | 80 | 70 | 27 | 28 | 48 | 31 | 33 |
| 2-(4-fluorophenyl)-4-(4-phenylphenyl)2,4-di- | 100 | 79 | — | 69 | 79 | 87 | 100 | 96 | 46 | 50 | 90 |
| methyl-2,4-disila-1-(1H-1,2,4-triazol-1-yl)pentane | 50 | 75 | — | 69 | 79 | 87 | 100 | 96 | 46 | 50 | 90 |
| 2-(4-ethoxyphenyl)-4-(4-fluorophenyl)-2,4-di- | 100 | 44 | 9 | 28 | 46 | 69 | 64 | 89 | 45 | 32 | 0 |
| methyl-2,4-disila-1-(1H-1,2,4-triazol-1-yl)pentane | 50 | 38 | 9 | 28 | 40 | 67 | 64 | 74 | 41 | 29 | 0 |
| 2,2-bis(4-fluorophenyl)-4,4-dimethyl-2,4- | 100 | 35 | 6 | 24 | 37 | 67 | 61 | 67 | 34 | 29 | — |
| disila-1-(1H-1,2,4-triazol-1-yl)pentane | 50 | 32 | 6 | 20 | 31 | 60 | 57 | 60 | 31 | 24 | — |
| 2,4-bis(4-fluorophenyl)-2-(4-phenylphenyl)-4- | 100 | 79 | — | 69 | 79 | 87 | 100 | 96 | 46 | 50 | 90 |
| methyl-2,4-disila-1-(1H-1,2,4-triazol-1-yl)pentane | 50 | 75 | — | 69 | 79 | 87 | 100 | 96 | 46 | 50 | 90 |
| 2,2-bis(4-ethoxyphenyl)-4-(4-fluorophenyl)-4- | 100 | 72 | 60 | 74 | 78 | 77 | 100 | 78 | 63 | 43 | 66 |
| methyl-2,4-disila-1-(1H-1,2,4-triazol-1-yl)pentane | 50 | 63 | 50 | 53 | 74 | 71 | 100 | 78 | 58 | 19 | 69 |
| 2,2-bis(4-fluorophenyl)-4-(4-phenylphenyl)-4- | 100 | 46 | 9 | 32 | 49 | 73 | 57 | 67 | 41 | 29 | 23 |
| methyl-2,4-disila-1-(1H-1,2,4-triazol-1-yl)pentane | 50 | 46 | 6 | 28 | 47 | 71 | 54 | 65 | 41 | 29 | 18 |
| 2,4-bis(4-fluorophenyl)-2-(4-phenylphenyl)-4- | 100 | 46 | 14 | 32 | 51 | 78 | 50 | 43 | 45 | 24 | 47 |
| methyl-2,4-disila-1-(1H-1,2,4-triazol-1-yl)pentane | 50 | 38 | 12 | 22 | 43 | 76 | 50 | 31 | 41 | 23 | 20 |
| 2,2-bis(4-chlorophenyl)-4-(4-fluorophenyl)-4- | 100 | 58 | 9 | 48 | 61 | 0 | 57 | 77 | 55 | 32 | 53 |
| methyl-2,4-disila-1-(1H-1,2,4-triazol-1-yl)pentane | 50 | 51 | 6 | 44 | 54 | 0 | 57 | 43 | 41 | 26 | 37 |
| 2-(4-chlorophenyl)-4-(4-ethoxyphenyl)-2-(4- | 100 | 79 | 25 | 69 | 79 | 87 | 100 | 96 | 46 | 50 | 90 |
| fluorophenyl)-4-methyl-2,4-disila-1-(1H-1,2,4-triazol-1-yl)pentane | 50 | 75 | 23 | 69 | 74 | 87 | 100 | 96 | 46 | 50 | 90 |
| 4-(4-chlorophenyl)-2,2-bis(4-fluorophenyl)-4- | 100 | 34 | 12 | 100 | 87 | 90 | 87 | 100 | 56 | 89 | 80 |
| methyl-2,4-disila-1-(1H-1,2,4-triazol-1-yl) | 50 | 32 | 10 | 80 | 76 | 87 | 76 | 100 | 45 | 78 | 76 |

TABLE 9-continued

The percent control of (1H-1,2,4-triazolyl)disilaalkane derivatives to fungi $$\begin{array}{c} R_3 \quad R_1 \\ R_4Si-CH_2Si-CH_2-N \\ R_5 \quad R_2 \end{array} \diagup \!\!\! \begin{array}{c} N \\ \diagdown N \end{array}$$

| Compounds | conc. (ppm) | Al. | Phy ca. | Phy ba. | Bo.do (Ma.) | Glo. | Py. or. | Rhy. so. | Fu. mo. | Rhi. sp. | Bo ci. |
|---|---|---|---|---|---|---|---|---|---|---|---|
| pentane | | | | | | | | | | | |
| 2,4-bis(4-chlorophenyl)-2-(4-methoxyphenyl)-4- | 100 | 89 | 65 | 79 | 79 | 87 | 100 | 92 | 48 | 50 | 43 |
| methyl-2,4-disila-1-(1H-1,2,4-triazol-1-yl) | 50 | 74 | 45 | 76 | 75 | 76 | 100 | 90 | 42 | 46 | 40 |
| pentane | | | | | | | | | | | |
| 2,2-bis(4-chlorophenyl)-4,4-dimethyl-2,4-di- | 100 | 79 | 34 | 100 | 72 | 89 | 95 | 66 | 65 | 54 | 85 |
| sila-1-(1H-1,2,4-triazol-1-yl)pentane | 50 | 75 | 28 | 90 | 70 | 83 | 90 | 56 | 46 | 51 | 67 |
| 4,4-tris(4-fluorophenyl)-6-methyl-4,6-di- | 100 | 72 | 60 | 74 | 78 | 77 | 100 | 78 | 63 | 43 | 66 |
| sila-7-(1H-1,2,4-triazol-1-yl)-1-heptane | 50 | 63 | 50 | 53 | 74 | 71 | 100 | 78 | 58 | 19 | 69 |
| 6,6-diphenyl-4-methyl-4,6-disila-4- | 100 | 89 | 40 | 100 | 100 | 100 | 100 | 100 | 100 | 100 | 100 |
| (1H-1,2,4-triazol-1-ylmethyl)-1,8-nonadiene | 50 | 72 | 33 | 84 | 80 | 89 | 100 | 80 | 60 | 50 | 77 |
| 6,6-bis(4-fluorophenyl)-4-methyl-4,6-disila- | 100 | 100 | 100 | 80 | 100 | 100 | 100 | 87 | 100 | 100 | 100 |
| 4-(1H-1,2,4-triazol-1-ylmethyl)-1,8-nonadiene | 50 | 78 | 21 | 60 | 100 | 100 | 85 | 75 | 100 | 100 | 86 |
| 6-(4-ethoxyphenyl)-4,4-bis(4-fluorophenyl)-6- | 100 | 100 | 90 | 75 | 69 | 80 | 75 | 100 | 90 | 90 | 60 |
| ethyl-4,6-disila-7-(1H-1,2,4-triazol-1-yl)-1- | 50 | 100 | 80 | 60 | 65 | 80 | 70 | 100 | 90 | 80 | 60 |
| heptane | | | | | | | | | | | |
| 6-(4-fluorophenyl)-4-methyl-6-(2-propenyl)- | 100 | 90 | 60 | 95 | 90 | 85 | 100 | 96 | 60 | 58 | 95 |
| 4,6-disila-4-(1H-1,2,4-triazol-1-ylmethyl)- | 50 | 78 | 55 | 90 | 79 | 82 | 100 | 96 | 60 | 56 | 90 |
| 1,8-nonadiene | | | | | | | | | | | |
| 6-(4-ethoxyphenyl)-6-methyl-4-phenyl-4-(4- | 100 | 100 | 70 | 100 | 100 | 90 | 85 | 100 | 80 | 75 | 85 |
| phenylphenyl-4,6-disila-7-(1H-1,2,4-triazol- | 50 | 100 | 60 | 100 | 100 | 80 | 75 | 100 | 80 | 75 | 80 |
| 1-yl)-1-heptane | | | | | | | | | | | |
| 4-methyl-6-bis(2-propenyl)-4,6-disila-4- | 100 | 95 | 50 | 85 | 75 | 87 | 100 | 96 | 65 | 80 | 80 |
| (1H-1,2,4-triazol-1-ylmethyl)-1,8-nonadiene | 50 | 75 | 45 | 80 | 70 | 82 | 100 | 96 | 46 | 60 | 60 |
| 6-(4-fluorophenyl)-4-methyl-6-phenyl-4,6-di- | 100 | 92 | 70 | 82 | 79 | 85 | 90 | 96 | 66 | 50 | 70 |
| sila-4-(1H-1,2,4-triazol-1-ylmethyl)-1,8- | 50 | 55 | 65 | 82 | 79 | 80 | 90 | 96 | 60 | 50 | 60 |
| nonadiene | | | | | | | | | | | |
| 4,6-bis(4-)-6-methyl-4-phenyl- | 100 | — | 68 | 74 | 78 | 77 | 100 | 78 | 63 | 43 | 66 |
| 4,6-disila-7-(1H-1,2,4-trizaol-1-yl)-1- | 50 | — | 56 | 53 | 74 | 71 | 100 | 78 | 58 | 19 | 69 |
| heptane | | | | | | | | | | | |
| 4-methyl-6-phenyl-6-(4-phenylphenyl)-4,6-di- | 100 | 100 | 60 | 100 | 100 | 100 | 100 | 100 | 100 | 56 | 100 |
| sila-4-(1H-1,2,4-triazol-1-ylmethyl)-1,8- | 50 | 72 | 38 | 84 | 100 | 100 | 100 | 80 | 100 | 40 | 77 |
| nonadiene | | | | | | | | | | | |
| 6-(4-fluorophenyl)-6-methyl-4-phenyl-4-(4- | 100 | 100 | 50 | 100 | 100 | 100 | 100 | — | 100 | 100 | 100 |
| phenylphenyl)-4,6-disila-7-(1H-1,2,4-triazol- | 50 | 78 | 27 | 100 | 100 | 100 | 85 | — | 100 | 100 | 86 |
| 1-yl)-1-heptane | | | | | | | | | | | |
| 6,6-bis(4-ethoxyphenyl)-4-methyl-4,6-disila- | 100 | 100 | 60 | — | 72 | 100 | 100 | 100 | 100 | 80 | 100 |
| 4-(1H-1,2,4-triazol-1-ylmethyl)-1,8-nonadiene | 50 | 100 | 55 | — | 70 | 100 | 100 | 100 | 100 | 80 | 100 |
| 6-phenyl-4,6-bis(2-propenyl)-4,6-disila-4- | 100 | 79 | 70 | 69 | 70 | 87 | 90 | — | 46 | 50 | 96 |
| (1H-1,2,4-triazol-1-ylmethyl)-1,8-nonadiene | 50 | 75 | 60 | 60 | 65 | 70 | 60 | — | 46 | 50 | 80 |
| 6-(4-fluorophenyl)-6-(4-phenylphenyl)-4-(2- | 100 | 100 | 50 | 100 | 100 | 100 | 100 | 100 | — | 100 | 100 |
| propenyl)-4,6-disila-4-(1H-1,2,4-triazol-1- | 50 | 100 | 40 | 100 | 100 | 100 | 100 | 100 | — | 100 | 100 |
| ylmethyl)-1,8-nonadiene | | | | | | | | | | | |
| 4,6-(4-fluorophenyl)-6-(4-phenylphenyl)-4,6- | 100 | 65 | 75 | 65 | 79 | 87 | 100 | 96 | 46 | 56 | — |
| disila-4-(1H-1,2,4-triazol-1-ylmethyl)-1,8- | 50 | 62 | 75 | 60 | 79 | 85 | 100 | 90 | 40 | 56 | — |
| nonadiene | | | | | | | | | | | |
| 4-(4-fluorophenyl)-6-phenyl-6-(4-phenylphenyl)- | 100 | 78 | 72 | 69 | — | 86 | 100 | 90 | 65 | 58 | 90 |
| 4,6-disila-4-(1H-1,2,4-triazol-1-ylmethyl)- | 50 | 72 | 70 | 65 | — | 80 | 100 | 60 | 61 | 50 | 90 |
| 1,8-nonadiene | | | | | | | | | | | |
| 4,4,4-tris(4-fluorophenyl)-6-methyl-4,6-di- | 100 | 72 | 60 | 74 | 78 | 77 | 100 | 78 | 63 | 43 | 66 |
| sila-7-(1H-1,2,4-triazol-1-yl)-1-heptane | 50 | 63 | 50 | 53 | 74 | 71 | 100 | 78 | 58 | 19 | 69 |
| 6,6-diphenyl-4-methyl-4,6-disila-4- | 100 | 89 | 40 | 100 | 100 | 100 | 100 | 100 | 100 | 100 | 100 |
| (1H-1,2,4-triazol-1-ylmethyl)-1,8-nonadiene | 50 | 72 | 33 | 84 | 80 | 89 | 100 | 80 | 60 | 50 | 77 |
| 6,6-bis(4-fluorophenyl)-4-methyl-4,6-disila- | 100 | 100 | 100 | 80 | 100 | 100 | 100 | 87 | 100 | 100 | 100 |
| 4-(1H-1,2,4-triazol-1-ylmethyl)-1,8-nonadiene | 50 | 78 | 21 | 60 | 100 | 100 | 85 | 75 | 100 | 100 | 86 |
| 6-(4-ethoxyphenyl)-4,4-bis(4-fluorophenyl)-6- | 100 | 100 | 90 | 75 | 69 | 80 | 75 | 100 | 90 | 90 | 60 |
| ethyl-4,6-disila-7-(1H-1,2,4-triazol-1-yl)-1- | 50 | 100 | 80 | 60 | 65 | 80 | 70 | 100 | 90 | 80 | 60 |
| heptane | | | | | | | | | | | |
| 6-(4-fluorophenyl)-4-methyl-6-(2-propenyl)- | 100 | 90 | 60 | 95 | 90 | 85 | 100 | 96 | 60 | 58 | 95 |
| 4,6-disila-4-(1H-1,2,4-triazol-1-ylmethyl)- | 50 | 78 | 55 | 90 | 79 | 82 | 100 | 96 | 60 | 56 | 90 |
| 1,8-nonadiene | | | | | | | | | | | |
| 6-(4-ethoxyphenyl)-6-methyl-4-phenyl-4-(4- | 100 | 100 | 70 | 100 | 100 | 90 | 85 | 100 | 80 | 75 | 85 |
| phenylphenyl-4,6-disila-7-(1H-1,2,4-triazol- | 50 | 100 | 60 | 100 | 100 | 80 | 75 | 100 | 80 | 75 | 80 |
| 1-yl)-1-heptane | | | | | | | | | | | |
| 4-methyl-4,6-bis(2-propenyl)-4,6-disila-4- | 100 | 95 | 50 | 85 | 75 | 87 | 100 | 96 | 65 | 80 | 80 |
| (1H-1,2,4-triazol-1-ylmethyl)-1,8-nonadiene | 50 | 75 | 45 | 80 | 70 | 82 | 100 | 96 | 46 | 60 | 60 |
| 6-(4-fluorophenyl)-4-methyl-6-phenyl-4,6-di- | 100 | 92 | 70 | 82 | 79 | 85 | 90 | 96 | 66 | 50 | 70 |
| sila-4-(1H-1,2,4-triazol-1-ylmethyl)-1,8- | 50 | 55 | 65 | 82 | 79 | 80 | 90 | 96 | 60 | 50 | 60 |
| nonadiene | | | | | | | | | | | |
| 4,6-bis(4-chlorophenyl)-6-methyl-4-phenyl- | 100 | — | 68 | 74 | 78 | 77 | 100 | 78 | 63 | 43 | 66 |
| 4,6-disila-4-(1H-1,2,4-triazol-1-yl)-1- | 50 | — | 56 | 53 | 74 | 71 | 100 | 78 | 58 | 19 | 69 |

TABLE 9-continued

The percent control of (1H-1,2,4-triazolyl)disilaalkane derivatives to fungi

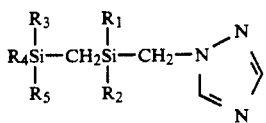

| Compounds | conc. (ppm) | Al. | Phy ca. | Phy ba. | Bo.do (Ma.) | Glo. | Py. or. | Rhy. so. | Fu. mo. | Rhi. sp. | Bo ci. |
|---|---|---|---|---|---|---|---|---|---|---|---|
| heptane 4-methyl-6-phenyl-6-(4-phenylphenyl)-4,6-di-sila-4-(1H-1,2,4-triazol-1-ylmethyl)-1,8-nonadiene | 100 | 100 | 60 | 100 | 100 | 100 | 100 | 100 | 100 | 56 | 100 |
| | 50 | 72 | 38 | 84 | 100 | 100 | 100 | 80 | 100 | 40 | 77 |
| 6-(4-fluorophenyl)-6-methyl-4-phenyl-4-(4-phenylphenyl)-4,6-disila-7-(1H-1,2,4-triazol-1-yl)-1-heptane | 100 | 100 | 50 | 100 | 100 | 100 | 100 | — | 100 | 100 | 100 |
| | 50 | 78 | 27 | 100 | 100 | 100 | 85 | — | 100 | 100 | 86 |
| 6,6-bis(4-ethoxyphenyl)-4-methyl-4,6-disila-4-(1H-1,2,4-triazol-1-ylmethyl)-1,8-nonadiene | 100 | 100 | 60 | — | 72 | 100 | 100 | 100 | 100 | 80 | 100 |
| | 50 | 100 | 55 | — | 70 | 100 | 100 | 100 | 100 | 80 | 100 |
| 6-phenyl-4,6-bis(2-propenyl)-4,6-disila-4-(1H-1,2,4-triazol-1-ylmethyl)-1,8-nonadiene | 100 | 79 | 70 | 69 | 70 | 87 | 90 | — | 46 | 50 | 96 |
| | 50 | 75 | 60 | 60 | 65 | 70 | 60 | — | 46 | 50 | 80 |
| 6-(4-fluorophenyl)-6-(4-phenylphenyl)-4-(2-propenyl)-4,6-disila-4-(1H-1,2,4-triazol-1-ylmethyl)-1,8-nonadiene | 100 | 100 | 50 | 100 | 100 | 100 | 100 | 100 | — | 100 | 100 |
| | 50 | 100 | 40 | 100 | 100 | 100 | 100 | 100 | — | 100 | 100 |
| 4,6-(4-fluorophenyl)-6-(4-phenylphenyl)-4,6-disila-4-(1H-1,2,4-triazol-1-ylmethyl)-1,8-nonadiene | 100 | 65 | 75 | 65 | 79 | 87 | 100 | 96 | 46 | 56 | — |
| | 50 | 62 | 75 | 60 | 79 | 85 | 100 | 90 | 40 | 56 | — |
| 4-(4-fluorophenyl)-6-phenyl-6-(4-phenylphenyl)-4,6-disila-4-(1H-1,2,4-triazol-1-ylmethyl)-1,8-nonadiene | 100 | 78 | 72 | 69 | — | 86 | 100 | 90 | 65 | 58 | 90 |
| | 50 | 72 | 70 | 65 | — | 80 | 100 | 60 | 61 | 50 | 90 |

What is claimed is:

1. A (1-H-1,2,4-triazolyl)disilaalkane compound represented by Formula I:

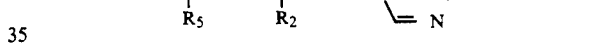

wherein $R_1$, $R_2$, $R_3$, $R_4$ and $R_5$ are independently selected from the group consisting of lower alkyl, vinyl, allyl, benzyl and substituted phenyl, wherein said phenyl is substituted with a radical selected from the group consisting of fluoro, chloro, methoxy, ethoxy and phenyl.

* * * * *